(12) United States Patent
Berrada et al.

(10) Patent No.: US 7,621,870 B2
(45) Date of Patent: Nov. 24, 2009

(54) EVERTED FILTER DEVICE

(75) Inventors: Marwane Berrada, White Bear Lake, MN (US); Richard Kusleika, Eden Prairie, MN (US); Kent Anderson, Champlin, MN (US)

(73) Assignee: EV3 Inc., Plymouth, MN (US)

( * ) Notice: Subject to any disclaimer, the term of this patent is extended or adjusted under 35 U.S.C. 154(b) by 667 days.

(21) Appl. No.: 11/208,497

(22) Filed: Aug. 22, 2005

(65) Prior Publication Data

US 2005/0283186 A1     Dec. 22, 2005

Related U.S. Application Data

(63) Continuation of application No. 10/096,624, filed on Mar. 12, 2002, now abandoned.

(51) Int. Cl.
*A61M 29/00* (2006.01)
(52) U.S. Cl. ..................................... 600/200
(58) Field of Classification Search ................ 606/159, 606/190–194, 200, 113, 114, 127, 128; 604/104–107
See application file for complete search history.

(56) References Cited

U.S. PATENT DOCUMENTS 5,071,407 A    12/1991    Termin et al.

(Continued)

FOREIGN PATENT DOCUMENTS

| WO | WO 96/01591 | 1/1996 |
| WO | WO 98/52475 | 11/1998 |
| WO | WO 99/12478 | 3/1999 |
| WO | WO 00/16705 | 3/2000 |
| WO | WO 00/53120 | 9/2000 |

(Continued)

OTHER PUBLICATIONS

U.S. Appl. No. 10/093,572, filed Mar. 8, 2002 (Ref. No. MVA1003US).

(Continued)

*Primary Examiner*—Todd E Manahan
*Assistant Examiner*—Jennifer L Hornberger
(74) *Attorney, Agent, or Firm*—Popovich, Wiles & O'Connell, P.A.

(57) ABSTRACT

Everting filter devices and methods for using the devices, including using the devices as intra-vascular filters to filter thrombus, emboli, and plaque fragments from blood vessels. The filter devices include a filter body nominally tubular in shape and having a large proximal opening. The filter body can extend from a proximal first end region distally over the non-everted exterior surface of the filter, further extending distally to a distal-most region, then converging inwardly and extending proximally toward the filter second end region, forming a distal everted cavity. The degree of eversion of the filter can be controlled by varying the distance between the filter first end region near the proximal opening and the closed second end region. Bringing the filter first and second end regions closer together can bring filter material previously on the non-everted filter exterior to occupy the distal-most region. The everting process can also bring filter material previously in the distal-most position further into the distal everted cavity. The filter devices can be used to remove filtrate from body vessels, with the filtrate eventually occluding the distal-most region. The filter can then be further everted, bringing fresh, unoccluded filter material into place to provide additional filter capacity. Some everting filters have the capability of switching between occluding and filtering modes of operation, thereby allowing a treating physician to postpone the decision to use filtering or occluding devices until well after insertion of the device into the patient's body.

29 Claims, 24 Drawing Sheets

U.S. PATENT DOCUMENTS

| | | | |
|---|---|---|---|
| 5,486,332 | A | 1/1996 | Kamiyama et al. |
| 5,496,277 | A | 3/1996 | Termin et al. |
| 5,814,064 | A | 9/1998 | Daniel et al. |
| 5,846,261 | A | 12/1998 | Kotula et al. |
| 6,050,972 | A | 4/2000 | Zadno-Azizi et al. |
| 6,066,149 | A | 5/2000 | Samson et al. |
| 6,129,739 | A | 10/2000 | Khosravi |
| 6,179,861 | B1 | 1/2001 | Khosravi et al. |
| 6,200,288 | B1 | 3/2001 | Heaton et al. |
| 6,203,561 | B1 | 3/2001 | Ramee et al. |
| 6,214,025 | B1 | 4/2001 | Thistle et al. |
| 6,214,026 | B1 | 4/2001 | Lepak et al. |
| 6,221,086 | B1 | 4/2001 | Forber |
| 6,245,089 | B1 | 6/2001 | Daniel et al. |
| 6,264,663 | B1 * | 7/2001 | Cano ............... 606/114 |
| 6,325,815 | B1 | 12/2001 | Kusleika et al. |
| 6,350,271 | B1 | 2/2002 | Kurz et al. |
| 6,361,545 | B1 | 3/2002 | Macoviak et al. |
| 6,391,044 | B1 | 5/2002 | Yadav et al. |
| 6,436,112 | B2 | 8/2002 | Wensel et al. |
| 6,485,501 | B1 | 11/2002 | Green |
| 6,605,102 | B1 | 8/2003 | Mazzocchi et al. |
| 7,094,249 | B1 | 8/2006 | Broome et al. |
| 2002/0026211 | A1 | 2/2002 | Khosravi et al. |
| 2002/0032460 | A1 | 3/2002 | Kusleika et al. |
| 2002/0062135 | A1 | 5/2002 | Mazzocchi et al. |
| 2002/0072765 | A1 | 6/2002 | Mazzocchi et al. |
| 2002/0087187 | A1 | 7/2002 | Mazzocchi et al. |
| 2002/0095172 | A1 | 7/2002 | Mazzocchi et al. |
| 2002/0095173 | A1 | 7/2002 | Mazzocchi et al. |
| 2002/0111648 | A1 | 8/2002 | Kusleika et al. |
| 2002/0123720 | A1 | 9/2002 | Kusleika et al. |
| 2002/0123765 | A1 | 9/2002 | Sepetka et al. |
| 2002/0133092 | A1 | 9/2002 | Oslund et al. |
| 2002/0138095 | A1 | 9/2002 | Mazzocchi et al. |
| 2002/0161394 | A1 | 10/2002 | Macoviak et al. |
| 2008/0119889 | A1 * | 5/2008 | Kusleika ............... 606/200 |

FOREIGN PATENT DOCUMENTS

| | | |
|---|---|---|
| WO | WO 01/08743 | 2/2001 |
| WO | WO 01/15629 A1 | 3/2001 |
| WO | WO 01/21100 A1 | 3/2001 |
| WO | WO 01/21246 | 3/2001 |
| WO | WO 01/80748 | 11/2001 |
| WO | WO 01/89413 | 11/2001 |
| WO | WO 02/11627 | 2/2002 |

OTHER PUBLICATIONS

U.S. Appl. No. 10/132,562, filed Apr. 25, 2002 (Ref. No. MVA1005US).

U.S. Appl. No. 10/194,355, filed Jul. 12, 2002 (Ref. No. MVA1007US).

U.S. Appl. No. 10/194,734, filed Jul. 12, 2002 (Ref. No. MVA1008US).

Claims for U.S. Appl. No. 10/607,328, filed Jun. 26, 2003, Mazzocchi et al. (Ref. No. MVA1001C8).

International Search Report for counterpart PCT application, PCT/US03/07412 (1 page).

Self-Expanding Endovascular Prosthesis: An Experimental Study, Radiology 1987; 164: 709-714 Rousseau et al.

U.S. Patent Application Publication No. 2002/0026211, Feb. 28, 2002, Khosravi et al.

US 6,348,062, 02/2002, Hopkins et al. (withdrawn).

* cited by examiner

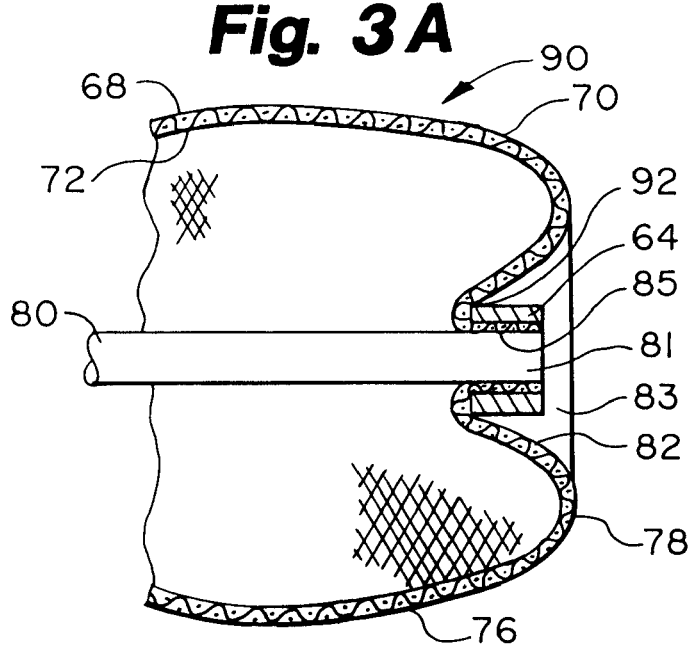
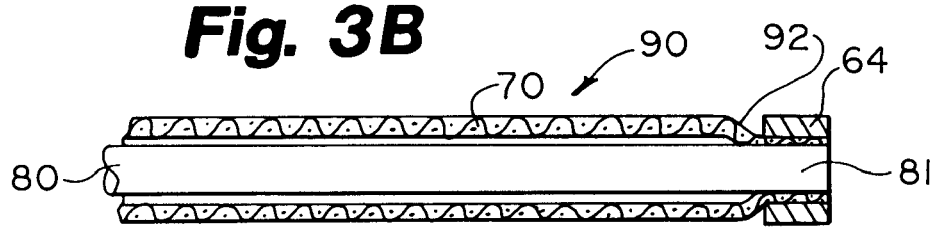
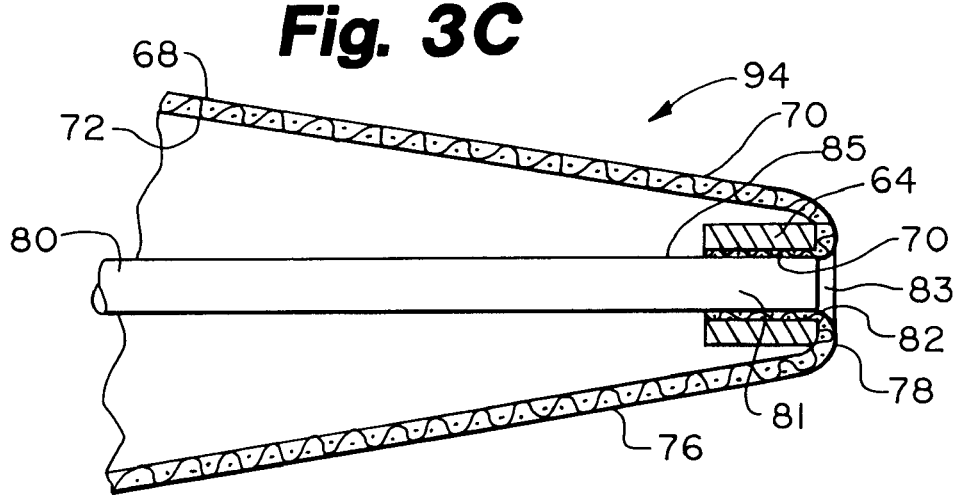

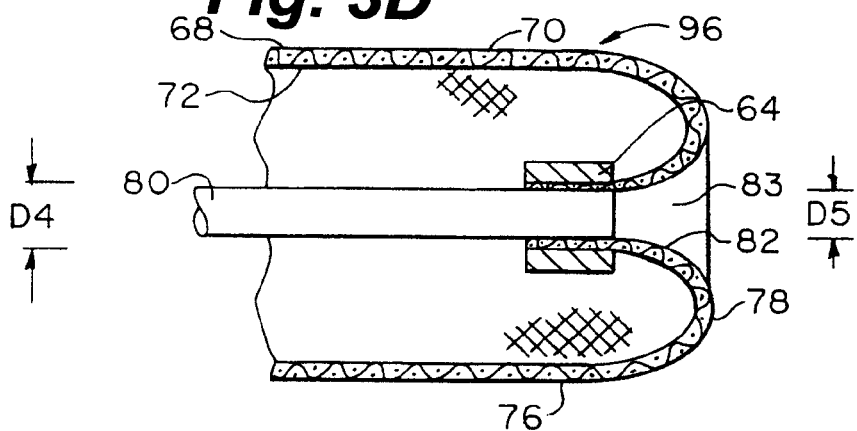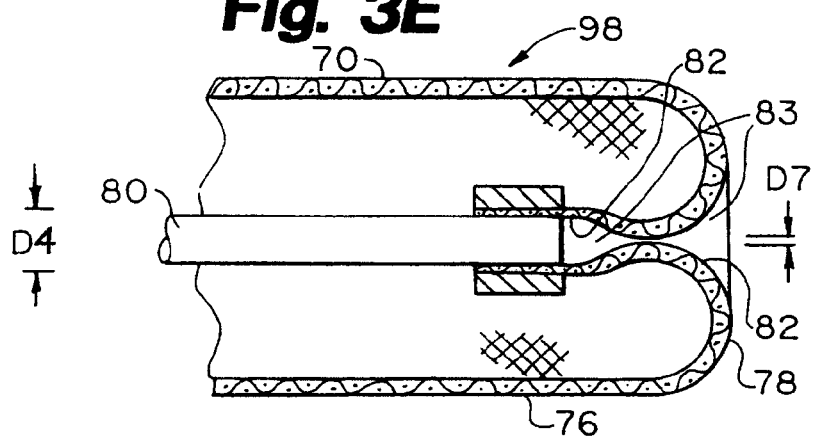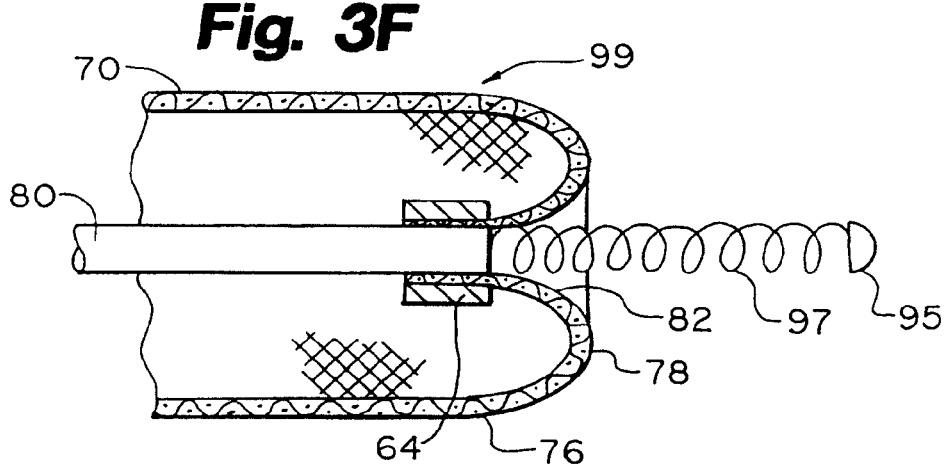

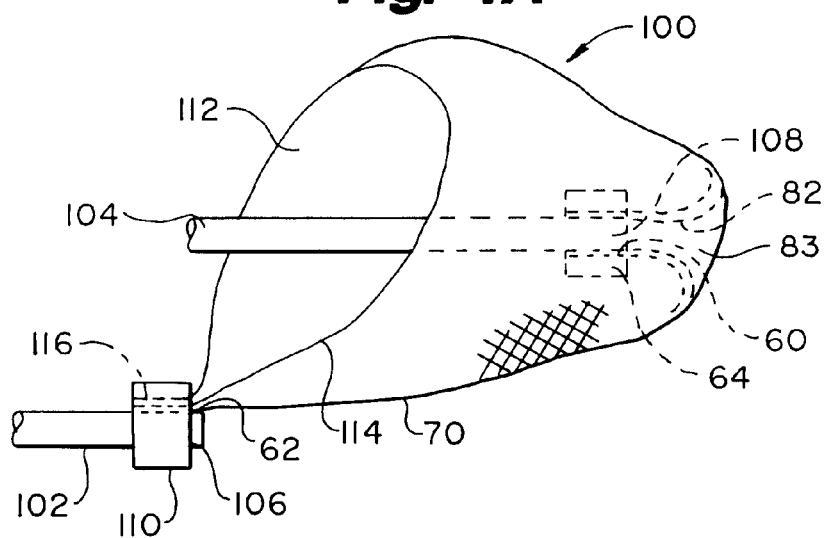
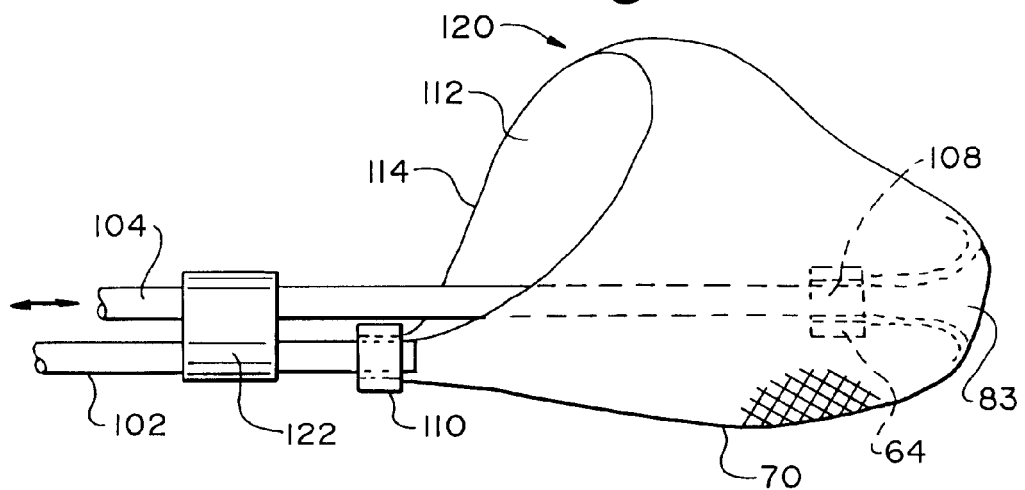

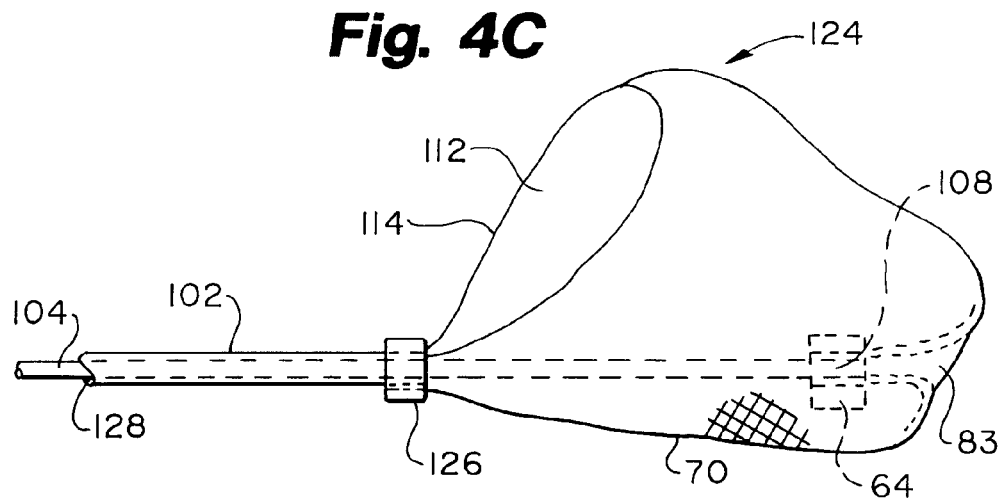
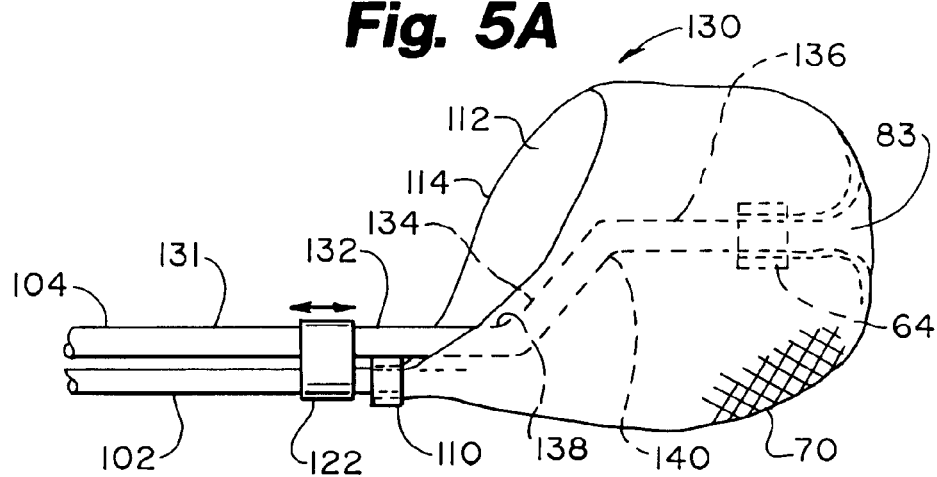

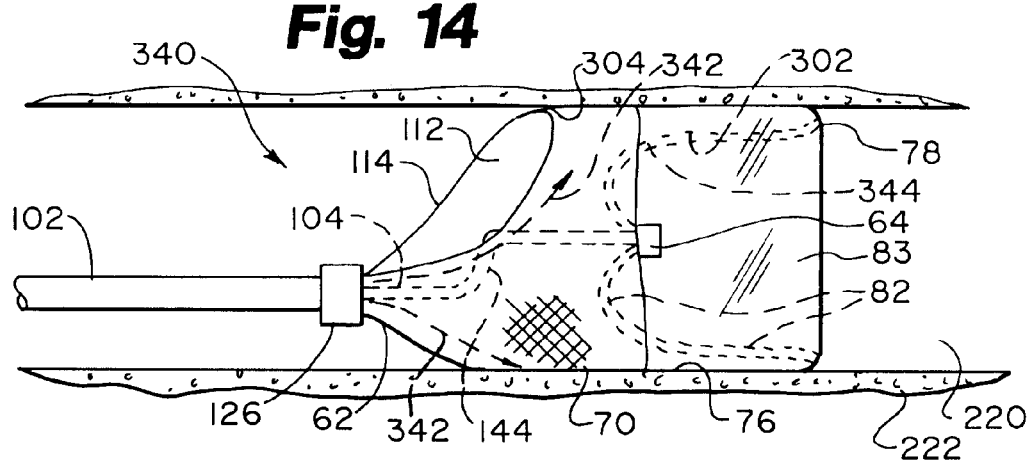

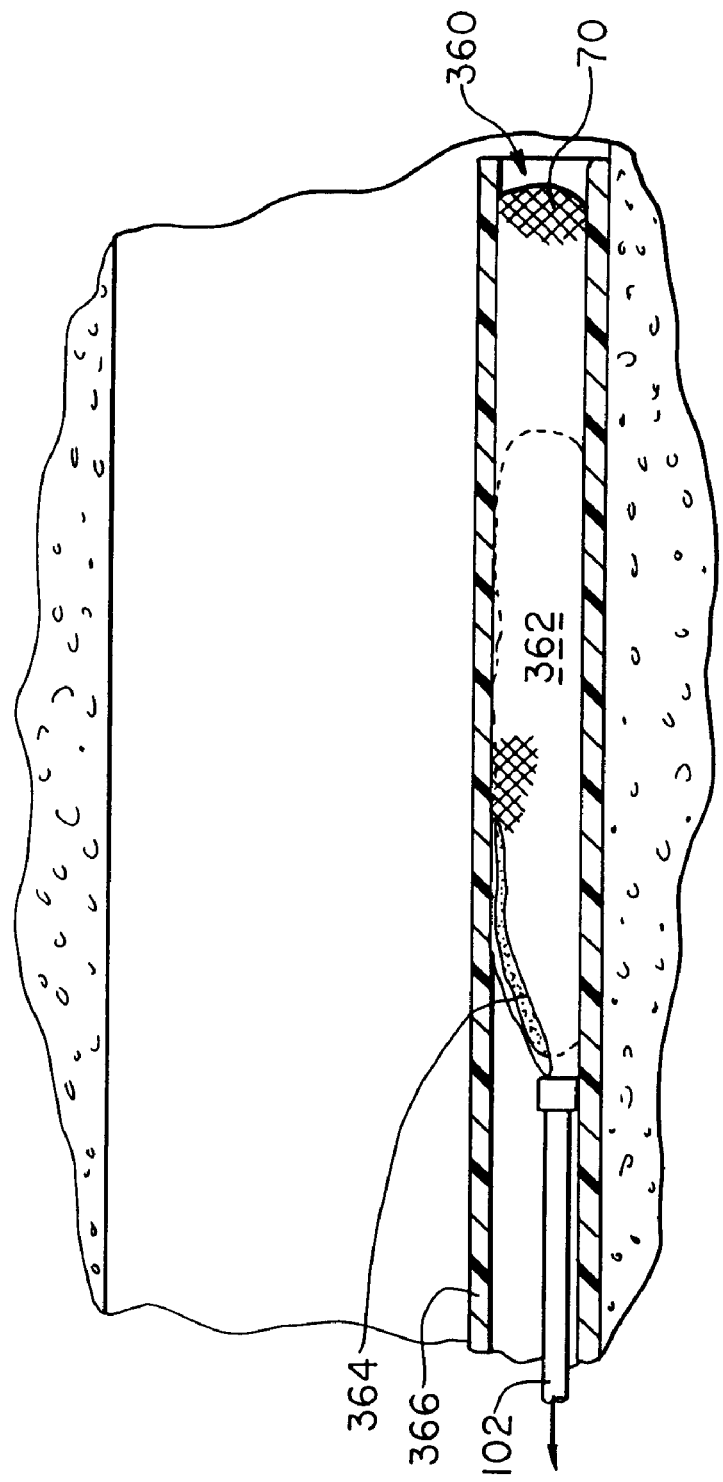

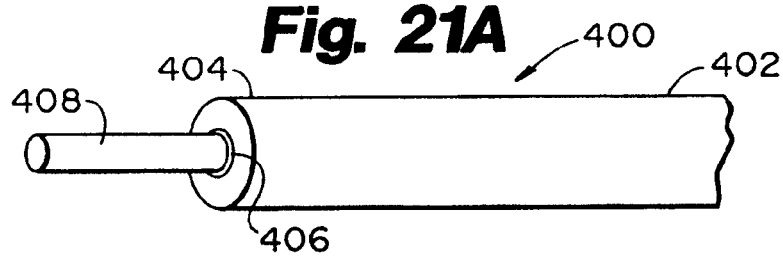
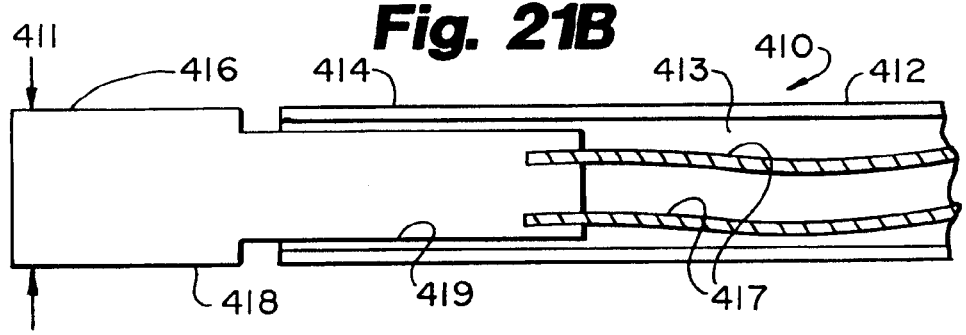
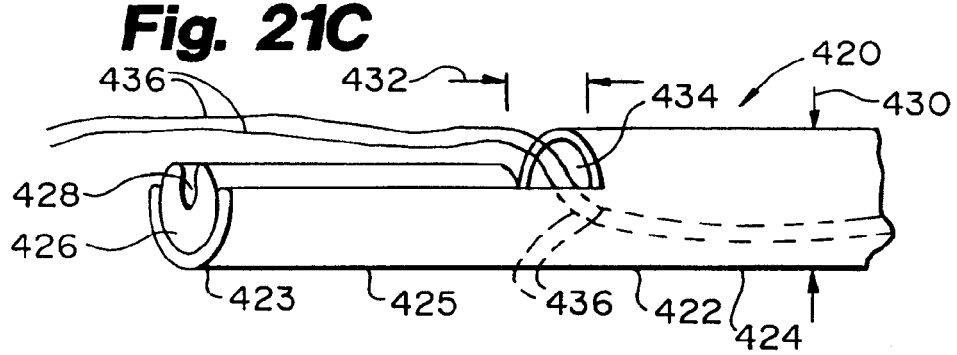
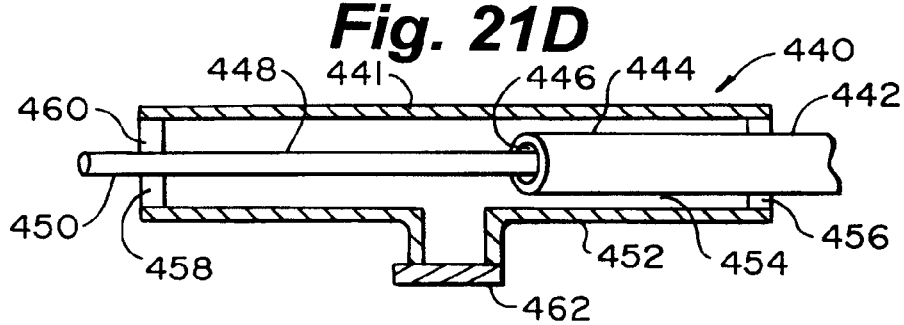

EVERTED FILTER DEVICE

CROSS-REFERENCE TO RELATED APPLICATION

This application is a continuation of U.S. application Ser. No. 10/096,624, filed Mar. 12, 2002 now abandoned, the contents of which are hereby incorporated herein by reference.

FIELD OF THE INVENTION

The present invention is related generally to medical devices. The present invention includes intravascular filter devices.

BACKGROUND OF THE INVENTION

Coronary vessels, partially occluded by plaque, may become totally occluded by a thrombus or blood clot causing myocardial infarction, angina and other conditions. A number of medical procedures have been developed to allow for the removal of plaque from vessel walls or to clear a channel through the thrombus or clot to restore blood flow and minimize the risk of myocardial infarction. Carotid, renal, peripheral, and other blood vessels can also be blocked and require treatment. For example, atherectomy or thrombectomy devices can be used to remove atheroma or thrombus. Alternatively, in percutaneous transluminal coronary angioplasty (PTCA), a guide wire or guide catheter is inserted into the femoral artery of a patient near the groin, advanced through the artery, over the aorta, and into a coronary artery. An inflatable balloon is then advanced into the coronary artery, across a stenosis or blockage, and the balloon inflated to dilate the blockage and open a flow channel through the partially blocked vessel region. While some stenoses remain in place once dilated, others are more brittle, and may partially crack and fragment, allowing the fragments to flow downstream where they may block more distal and smaller coronary vessels, possibly causing myocardial infarction, from that site. Consequences of embolization include stroke, diminished renal function, and impairment of peripheral circulation possibly leading to pain and amputation.

Saphenous vein grafts are often used to bypass occluded coronary vessels in coronary artery bypass surgery. With time, the grafts can become occluded with grumous. The grumous can also be dilated with balloons or removed in other ways. The grumous can present an even more difficult material to remove than thrombus, as the material is very friable, and likely to break into smaller fragments during the removal procedure.

Distal embolic protection devices have been developed to prevent the downstream travel of materials such as thrombi, grumous, emboli, and plaque fragments. Devices include occlusive devices and filters. Occlusive devices, for example distal inflatable balloon devices, can totally block fluid flow through the vessel. The material trapped by the inflatable devices can remain in place until removed using a method such as aspiration. However, aspiration cannot remove large particles because they won't fit through the aspiration lumen. Also, aspiration is a weak acting force and won't remove a particle unless the tip of the aspirating catheter is very close to the particle to be removed. During the occlusion, the lack of fluid flow can be deleterious. In coronary applications, the lack of perfusing blood flow can cause angina. In carotids, seizure can result from transient blockage of blood flow. In both coronaries and carotids it is not possible to predict who will suffer from angina or seizure due to vessel occlusion. If a procedure is started with an occlusive device, it may be necessary to remove it and start over with a filter device.

Some distal embolic protection devices include filters. The filters can be advanced downstream of a site to be treated and expanded to increase the filter area. Filtrate, such as emboli, can be captured in the filter until the procedure is complete or the filter is occluded. When the capacity of the filter is reached, the filter becomes occluded, blocking fluid flow past the filter device. The filter may then be retracted and replaced or left as is. If the filter is replaced with a fresh unoccluded filter, extra wire motions are required along with extra time. While the replacement is occurring, there is a period of no embolic protection for the patient and a risk of dislodging emboli during filter manipulation. If the filter is left in place, the vessel will be occluded during the remainder of the procedure and the patient can suffer the consequences of occlusion described earlier. Both choices are less than optimal.

Another shortcoming of current filters relates to their use distal of emboli sources when the emboli sources are located immediately proximal of a vessel bifurcation or trifurcation. Multiple filters may be required, one for each vessel branch, which is cumbersome and may not be done well, if attempted at all. Further, the use of multiple filters may not be compatible with other needed equipment such as angioplasty balloons and/or stents.

Some physicians prefer to use filters while others prefer to use occlusive devices. Whether a particular procedure may call for use of an occlusive device or a filter device may not be known until midway through the procedure. Occlusive distal protection devices are generally preferred for use in carotid vessels where even tiny particles can cause big problems if they happen to lodge in a very important but small artery. However, occlusive devices compromise fluoroscopic imaging due to the lack of flow during radiopaque dye injection.

What would be desirable are intravascular filters capable of additional filtering after being occluded with thrombi, without being removed from the body. What would be advantageous are intravascular filters which can be manipulated between a filtering mode and an occluding mode. Filters that can be used in the vicinity of a bifurcation would be beneficial.

SUMMARY OF THE INVENTION

The present invention provides everted filter trap devices and methods for using the everted filters. The devices can be used in body vessels including the coronary, carotid, renal, neurological and cerebral blood vessels, as well as ureters, and the respiratory and biliary tracts.

The everted filters can include a tubular filter body having a large proximal opening and a closed distal end. The filter body can extend distally from a first end region near the filter body proximal opening, further extending over an intermediate, non-everted region, continuing distally and everting over a distal-most region. The everting causes the filter body exterior to converge inwardly and proximally to a closed, filter body second end region. The proximally extending and inwardly converging exterior surface of the filter body defines a distal, everted cavity bounded distally by the distal-most extent of the everting filter. The distal everted cavity has exterior cavity walls which extend proximally back towards the proximal opening. The degree of eversion of the filter body may be changed through controlling the relative positions of the filter body first and second end regions. When the filter body diameter is held constant, proximally withdrawing the everted second end region toward the first end region increases the degree of eversion, increasing the distal everted cavity volume and length and increasing the length of filter body exterior surface within the distal, everted cavity.

In use, an everting filter device can be advanced to a target region within a body vessel region to be filtered. Some everting filter devices can be advanced over a guide wire, while other devices can be advanced in a constrained state within a delivery sheath. The everting filter body is preferably biased to expand radially outward to approach the target region vessel walls. The everting filter can be initially deployed in a minimally everted configuration, having a small distal everted cavity volume and length. With time, the everting filter interior surface near and around the filter distal-most region may become occluded with filtrate material. The everting filter may then be further everted, by bringing the filter body first and second end regions closer together. This relative movement can bring the occluded body material previously in the distal-most position to a position within the distal everted cavity sidewalls. This relative movement also brings filter material previously on the outside, non-everted surface region of the filter to the distal-most position, thereby providing fresh, non-occluded filter material.

The everting filter can provide fresh, porous, non-occluded filter material while proximally relocating the occluded filter material so that the perfusing vessel fluid flow is directed sideways over the occluded material rather than directly into the material. When the everting filter capacity is reached or the filtering is otherwise complete, the filter can be proximally retracted within a filter capture device, for example, a sheath. The captured, filtrate containing filter can then be withdrawn from the patient's body.

Some everting filter devices have a first, proximal shaft coupled to the filter body first end region and a second, distal shaft coupled to the filter body second end region, allowing the relative and absolute movements of the filter body end regions to be independently controlled. In some filter bodies, the distal shaft can be slidably disposed within the proximal shaft. In some embodiments, the distal shaft has a lumen for passing a guide wire therethrough. Some everting filter devices have only a single shaft coupled to the filter body second end region in the distal everted cavity. Such everting devices can rely on the radially outward expansion of the filter body against the vessel walls to anchor the filter body. The relative movement of the single shaft and coupled everted distal end of the filter body can control the degree of eversion by moving the single shaft relative to the anchored filter body.

Some everting filter devices can operate as filtering/occluding devices. One group of such devices have a filter body which includes an occluding portion and a filtering portion. The device can be operated in filtering mode by bringing the filtering portion to the distal-most region of the filter. The occluding mode can be attained by bringing the occluding portion of the filter body to the distal-most region. Some devices have a proximal filtering portion followed by a more distal occluding portion, while other devices have a proximal occluding portion followed distally by a filtering portion. The degree of eversion can control whether the filtering portion is disposed about the outside circumference of the filter body, in the distal-most region, or within the everting distal cavity to form the side walls. Such occluding/filtering devices can allow postponing the decision to use a filtering device or an occluding device past the time of deploying the device within the patient's vessel.

Other everting filter devices can be used as thrombectomy devices. The thrombectomy devices preferably have a large proximal opening and a proximal hoop or loop disposed near the proximal opening. The proximal loop can be stiff and attached to the filter body near the proximal opening. The thrombectomy device can be deployed distally of a thrombus, then retracted proximally through the thrombus, with the proximal loop dislodging the thrombus from the vessel wall. The thrombus can be captured within the filter body interior, with the filter body elongated during the capture. One mode of elongation begins with a highly everted filter body and then decreases the degree of eversion by proximally retracting a shaft coupled to the filter body proximal end region. The thrombectomy device carrying the thrombus can later be retracted within a tubular capture device.

Filters according to the present invention can be used to filter vessel regions immediately proximally upstream of a vessel bifurcation or trifurcation. In one method, the everted filter is advanced to the region in an elongated, radially reduced state, then more fully everted, expanding the filter exterior non-everted walls against the vessel interior walls. The filter can be both radially expanded and longitudinally shortened to approach and benignly anchor the filter to the vessel walls, providing coverage across the vessel proximal of the bifurcation. The filter effectively covers all the vessel branches distal of the branching, providing protection. The filter can be located in the region distal of the trunk but proximal of the branches.

Everted filters also have the advantage of rendering the filter relatively independent of the guide wire to prevent unwanted movement of the filter during motion of the guide wire. In some methods, the everted filter devices are used primarily to provide distal embolic protection and are advanced over a guide wire, where the guide wire can have another device advanced over the guide wire proximal of the filter. In other methods, the additional proximal device is used to remove or dilate plaque or thrombus, where the device is advanced over the filter shaft or tube, which is advanced over the guide wire. As the proximal device is exchanged over the guide wire, force is brought to bear on the guide wire, which can dislodge the guide wire and the filter. The everted filter has the advantage of rendering the filter comparatively insensitive to guide wire motion, so that guide wire movements do not as easily dislodge the filter. In particular, sliding, translational movements of the guide wire through an everted filter band of the present invention do not apply significant force on the filter. In one method, an everted filter is used as the distal end to a guide wire, where the filter is used primarily as a distal guide wire anchoring device. In another method, the filter has a tubular shaft, and the guide wire passes through the tube.

The everted filters also provide a filter device able to significantly increase the interior volume of the filter after positioning the filter in a vessel region. An everted filter can be advanced to a vessel site in a compressed state, having a small volume, small profile, and a high strand density due to a small inter-strand distance and pore size. In place, the filter can be both elongated and radially expanded to decrease the strand density and increase the pore size and filter interior volume.

DESCRIPTION OF THE DRAWINGS

FIG. 3A is a fragmentary, longitudinal, cross-sectional view of an everted filter device everted distal region, having the filter body interior surface secured to the shaft distal region, with the filter body biased to evert;

FIG. 3B is a fragmentary, longitudinal cross-sectional view of the everted filter device of FIG. 3A, shown in a small profile, elongated configuration;

FIG. 3C is a fragmentary, longitudinal, cross-sectional view of an everted filter device distal region having the filter body exterior surface mated to the shaft and having a conical shape;

FIG. 3D is a fragmentary, longitudinal, cross-sectional view of an everted filter device distal region having the filter body exterior surface mated to the shaft distal region and having a separated, diverging everted distal cavity;

FIG. 3E is a fragmentary, longitudinal, cross-sectional view of an everted filter device distal region having the filter body exterior mated to the shaft external surface and having a less separated, converging everted distal cavity;

FIG. 3F is a fragmentary, longitudinal, cross-sectional view of the everted filter device of FIG. 3D, having an atraumatic tip;

FIG. 4A is a fragmentary, perspective view of an everted filter device having a proximal shaft secured to a filter body proximal region and a distal shaft secured to the filter body distal region;

FIG. 4B is a fragmentary, perspective view of an everted filter device having a proximal shaft coupled to the filter body proximal region and the distal shaft coupled to the filter body distal region, with the distal shaft slidably coupled to the proximal shaft through a collar;

FIG. 4C is a fragmentary, perspective view of the distal portion of an everted filter device having a proximal shaft secured to the filter body proximal region and the distal shaft secured to the filter body distal region, with the distal shaft slidably received within a lumen in the proximal shaft;

FIG. 5A is a fragmentary, perspective view of a filter trap similar to that of FIG. 4B, but having a curved distal shaft extending transversely away from the proximal shaft;

FIG. 14 is a fragmentary, perspective view of a drug delivery catheter sharing some features with the device of FIG. 12A;

FIG. 19 is a fragmentary, longitudinal, cross-sectional view of the thrombectomy device and capture tube of FIG. 18, after the thrombectomy device and captured thrombus has been fully retracted within the capture tube;

FIGS. 21A-21F are fragmentary, longitudinal cross-sectional views of proximal portions of some embodiments of the invention.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims which follow.

Figure 1:
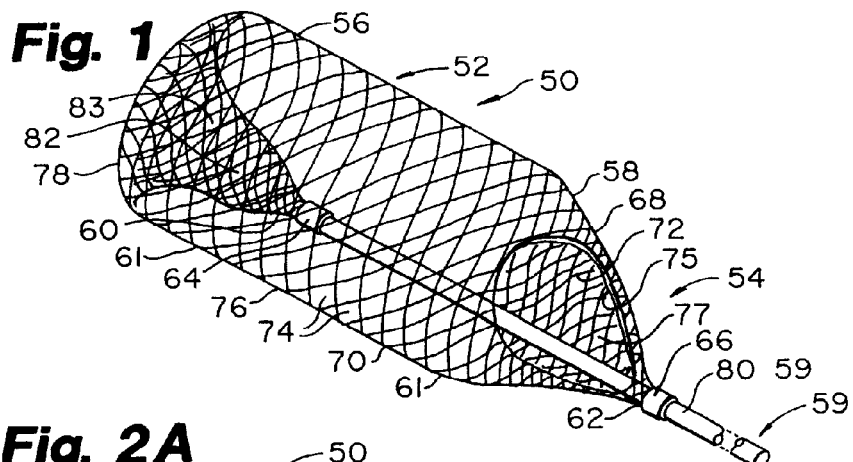
FIG. 1 is a perspective view of the distal portion of an everted filter device having a filter body, a shaft, an everted distal-most region, a fixed distal band, and an axially slidable proximal band.

FIG. 1 illustrates the distal portion of an everting filter 50. Everting filter 50 may be viewed as having a distal portion 52 and an intermediate portion 54. Distal portion 52 may be further divided into a distal portion distal region 56 and a distal portion proximal region 58. The device can extend proximally to a proximal portion 59.

Everting filter 50 includes a flexible, mesh, filter body 70. Filter body 70 may be formed of a plurality of wires or strands which can be used to form the mesh filter body through a variety of methods, for example, braiding, knitting, weaving, helically winding, and counterwinding. The mesh can be fused at some or all of the fiber or strand intersection points. The mesh can also be electrospun, and formed of sheet or film having holes formed by laser drilling, punching, dissolving components selectively, and the like. The strands can be formed of material such as wire, which can be metallic wire or polymeric wire. The wire may be substantially circular in cross section or may have any number of square, rectangular or irregular cross sectional profiles.

The mesh is preferably self-expanding. The self-expanding mesh can be formed totally or in part from self-expanding Nitinol, Elgiloy, titanium, or stainless steel wires and the like, and combinations thereof. The self-expanding mesh can also be formed of engineering polymers, for example, liquid crystal polymer, PEEK, polyimide, polyester, and the like. A preferred mesh is formed of Nitinol wires, which can be heat set to the desired expanded shape. The mesh can preferably be heat set to a desired bias shape using methods such as those disclosed in WO 96/01591, herein incorporated by reference. Another mesh is highly elastic, and preformed by mechanical overstress to the desired expanded shape. The mesh is preferably made radiopaque by means of plating, core wires, tracer wires, or fillers that have good X-ray absorption characteristics compared to the human body The mesh may be either partly or totally radiopaque.

Filter body 70 may be seen to have a plurality of pores or openings 74 between the filter body strands or wires. The pores have an average pore size over the filter body, where the individual pore sizes may vary depending upon the location over the filter body. Filter body 70 also has a proximal opening 77 formed in filter body proximal region 58 using techniques such as those disclosed in U.S. Pat. No. 6,325,815 (Kusleika et al.), which is herein incorporated by reference. Filter body 70 may also be considered to have an interior within the filter body and an exterior defined outside of the filter body. Filter body 70 further includes an interior surface 72 and an exterior surface 68. Filter body 70 may be seen to extend from a first end region 62 to a second end region 60. Filter body 70 includes an intermediate region 61 disposed between first end region 62 and second end region 60. Filter body proximal opening 77 may be seen to have a proximal opening mouth region 75 forming the circumference of the opening.

An elongate shaft 80 may be seen to extend distally from proximal region 59 and further distally within filter body 70. Unless otherwise noted, shafts in the present invention may be considered to be elongate members generally, being tethers, solid shafts, and tubes in various embodiments. Shaft 80 is a solid shaft in one embodiment, and can have at least one lumen therethrough, forming a tube, in other embodiments.

Shafts can be metallic, and formed of Nitinol, stainless steel, Elgiloy or other springy materials, mono-filament or multi-filament, for example, stranded or cable. The shafts can be tapered or have a uniform diameter over their length. Shafts can have a circular, flat, or other cross-sectional shape. The shafts can be single member or multi-member, for example, parallel independent structures. Shafts can be coiled and polymer coated as well as tubular and having a slippery coating.

Some shafts are entirely polymeric, for example, formed of engineering polymer, PEEK, polyimide, polyester, PTFE, and the like. Polymeric shafts can be reinforced with metals or stiff polymers in the form of braids, coils, sheets, ribbons, and the like. Shafts can be partly or entirely constructed of ceramics.

Filter body 70 can be slidably coupled to shaft 80, for example, by a proximal band, ring, bushing or collar 66, typically formed of metal and preferably radiopaque. In some embodiments, the slidably mounted bands or rings have a lubricious interior, and can be formed in part or totally from PTFE. Filter body second end region 60 can be axially, fixedly attached to shaft 80 with a distal band, ring, or collar 64. Filter body 70 has an everted shape. The everting aspect of filter body 70 may be considered to divide the filter body exterior surface into a non-everted region 76, proceeding to a distal-most region 78, proceeding further over the surface to an everted surface region 82. The everted shape of filter 70 defines an everted cavity or concave region 83 bounded by filter body everted surface region or cavity side walls 82 and the filter body distal-most extent. It may be seen from inspection of FIG. 1 that axially translating proximal ring 66 relative to distal ring 64 while holding the filter body diameter consistent may change the degree of eversion of filter body 70. The filter material occupying distal-most region 78 may therefore change with the degree of eversion of filter 70, with different locations of filter body 70 being distal-most varying as a function of the degree of eversion. The length of a distal cavity 83 will increase with increasing eversion.

The everting nature of the filter bodies may be further understood with reference to a common article of clothing, a sock. A sock may be removed, allowed to hang toe downward, a hand inserted within the interior, the distal toe region pinched with fingers from within, and the pinched region pulled upward, forming an everted toe region which is pulled inside out to form an exterior distal cavity or dimple near the closed end of the sock. The open end of the sock has a proximal opening bounded by a proximal mouth region. The degree of eversion of the sock may be increased by moving the pinched region upward or the open end downward, increasing the amount of material within the distal exterior cavity. The term filter sock may be used interchangeably with filter body in describing and claiming the present invention.

Figure 2A:
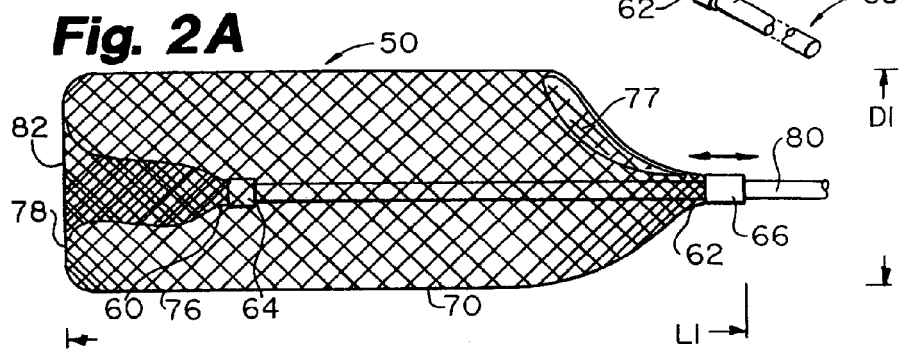
FIG. 2A is a side view of the everting trap of FIG. 1.

FIG. 2A illustrates everting filter body 70 from the side in a first configuration. Filter body 70 has a diameter indicated by D1 and a length L1. Filter body non-everted exterior surface 76, distal-most exterior surface region 78, and everted surface region 82 is as previously discussed with respect to FIG. 1. The relative locations of filter body first end region 62 and second end region 60 may be noted.

Figure 2B:
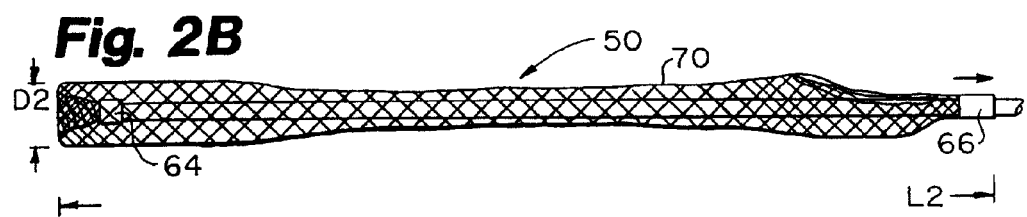
FIG. 2B is a side view of the everting trap of FIG. 1, shown in an elongated configuration having the proximal band slid proximally away from the distal band of FIG. 2A.

FIG. 2B further illustrates filter body 70 in a more elongated configuration relative to that of FIG. 2A. Filter body 70 has a diameter as indicated at D2 and a length as indicated at L2. It may be seen from inspection of FIG. 2B that diameter D2 is smaller than that of FIG. 2A and length L2 is greater than that of FIG. 2A. The configuration of FIG. 2B illustrates the elongatable nature of the filter body, which can be used to decrease the profile. The decreased profile configuration can be used to dispose the radially reduced filter body within filter delivery devices and tubes. The radially reduced aspect may also be used to insinuate the filter into small diameter body vessels, for example, distal blood vessels.

Figure 2C:
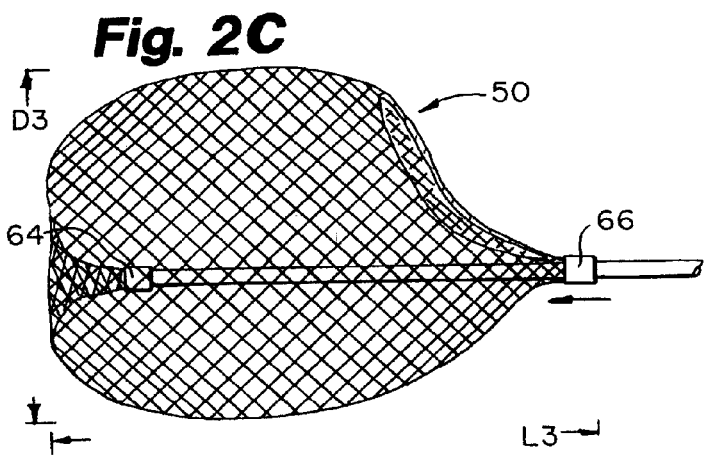
FIG. 2C is a side view of the everted filter device of FIG. 2A, shown in axially foreshortened configuration, having the proximal band slid distally toward the distal band of FIG. 2A.

FIG. 2C further illustrates filter body 70 in yet another configuration. In FIG. 2C, filter body 70 has a diameter D3 greater than that of FIG. 2A, and a length L3, less than that of FIG. 2A. The configuration of filter body 70 in FIG. 2C illustrates one configuration which may be used to expand the diameter of the filter to occupy a body conduit or vessel when the filter body is to be expanded against the vessel walls to substantially preclude fluid flow from bypassing the filter. The axial translation of proximal ring 66 relative to distal ring 64 may be seen to have varied both the length and diameter of the vessel in FIGS. 2A-2C. It may be seen from inspection of FIG. 2A that distally translating proximal ring 66 relative to distal ring 64 can also increase the degree of eversion of filter body 70, rather than increasing the diameter. This aspect of the invention will be discussed further.

Referring again to FIG. 1, one method forming the everted filter shape may be further discussed. Everting the filter can include everting the distal region of the filter body material to form the everted distal cavity bounded by the filter body exterior surface, as previously discussed. The filter body exterior surface may then be disposed around the exterior surface of the shaft distal end. The filter material exterior surface can then be operably coupled or mated to the shaft distal end exterior surface. The coupling of the filter exterior surface to the shaft may be accomplished by any method suitable for the filter body material. Various materials may be suitable for fixing using welding, braising, soldering, solvent welding, adhesives, and crimping. The filter body may also be fixed to the shaft using a band, for example, distal band 64 previously discussed. In a preferred embodiment, distal band 64 and the second end region of the filter body are fixed with respect to translation and rotation relative to shaft 80. In one embodiment, distal band 64 is fixed only with respect to translation, being allowed to rotate about shaft 80. This can be accomplished, for example, by enlarging the extreme distal end of shaft 80 to be larger than the inside diameter of distal ring 64. This method of everting the filter body may be seen from inspecting FIG. 1.

Proximal ring 66 may be used in various ways to slidably couple body first end region 62 to shaft 80. In one embodiment, proximal ring 66 is used to gather together and bind the extreme proximal end of a cylindrical tube of filter material, where the filter material can be fixed or adhered to the ring interior, and even folded back distally over the ring exterior and secured to the ring exterior using adhesion or further crimping. In some embodiments, the filter material itself slides axially over the shaft, being gathered and held in place by the proximal ring.

Filter body 70, along with first end region 62, second end region 82, distal cavity 83, distal-most region 78, non-everted region 76, and proximal opening 77 is used to refer to parts of the everting filters generally. The same reference numbers are used to refer to these locations for different filters, even though the filters are not identical and the same reference numerals may reference slightly different physical elements of different filters. It should also be understood that distal-most region 78 is used to refer to a region having an area and a length, rather than a point of tangency. The distal-most region may often refer to an annular shape having a cross-sectional area at least about half the cross sectional area of the filter at its widest part.

Referring again to FIGS. 2A-2C, one use of the everted filter to protect bifurcated and trifurcated vessel may be discussed. Filter body 70 has an elongated shape and small profile in FIG. 2B, which can be used to advantage to advance the filter to a vessel site through narrowed vessel regions, for example, past a stenosed vessel region. Once in position, a wide profile to occupy the entire vessel cross section is desirable, as is a large interior collection volume for the filter. The filter can be made to assume a wide profile by bringing the filter first and second end regions together to shorten the filter length and increase the filter outer diameter. Such a shape maybe seen in FIG. 2C.

In one use, filter body 70 can be advanced past a treatment site that is located immediately proximal of a bifurcation or trifurcation. The filter can be expanded to the bifurcation and then expanded to both deploy the filter material across all the branch vessels and to increase the collection volume of the filter, as in FIG. 2C.

Filter body 70 in FIG. 2C also illustrates another advantage of the present invention. A large profile filter body 70 can be used to anchor the filter against the interior vessel walls to stabilize the position of the filter. A guide wire can be passed through a lumen in shaft 80, and may continue distally past distal cavity 83. Proximal of filter body 70, other devices such as angioplasty devices, guide catheters, and atherectomy devices may be removed over the guide wire and replaced with other devices also passed over the guide wire. This use of the guide wire can act to dislodge the guide wire, which may have taken significant time and effort to position correctly. The movement of the guide wire can also dislodge previous filter devices passing over the guide wire. The anchoring of filter body 70 against the vessel walls allows a guide wire to pass through a lumen in the filter device, with the filter body being able to remain in place and resist movement caused by the guide wire. Another way to accommodate wire motion is for the wire motion to cause more or less filter eversion. The length of non-everted region 76 may vary in response to wire motion, but the proximal portion of non-everted region 76 will contact the vessel wall at an unmoving position.

FIG. 3A illustrates an alternate embodiment in the present invention for forming an everting filter 90, with the distal region only being shown. In the embodiment of FIG. 3A, the filter everting is accomplished by biasing the filter body 70 to assume an everted shape when unconstrained. The bias to assume the everted shape may be provided by heat setting the material to assume the everted shape when unconstrained. In one example, Nitinol wire braid can be heat set to assume the shape shown in FIG. 3A when not constrained by a surrounding delivery tube, and to assume the shape shown in FIG. 3B when constrained by extreme proximal tension put on filter body 70 from the proximal end. Everting filter 90 may be seen to share some aspects of the invention previously discussed. Filter body 70 may be seen to have interior surface 72 and exterior surface 68. Filter body 70 may be seen to extend from noninverted region 76, to a distal-most region 78, and further to everted region 82. Everted region 82 defines an everted cavity or concave region 83 within, bounded by distal-most region or extent 78. In FIG. 3A, shaft 80 may be seen to have a distal end region 81 having a shaft exterior surface 85 thereabout. Filter body 70 may be seen to have interior surface 72 which is mated about shaft distal end 81, to exterior surface 85. The filter body interior surface can thus face the shaft exterior surface directly. In the example illustrated, distal ring 64 is disposed about filter body 70 and shaft distal end region 81. A proximal-most extent of everted cavity 83 is indicated in FIG. 3A at 92.

FIG. 3B illustrates everting filter 90 of FIG. 3A, in a reduced profile configuration. Filter body 70 has been proximally retracted from distal ring 64. The configuration of FIG. 3B may be understood to be a constrained configuration, maintained only by proximally drawing filter body 70 and preventing filter body 70 from freely assuming the unconstrained configuration illustrated in FIG. 3A. The location 92, previously the proximal-most extent of the everted cavity of FIG. 3A may be noted in FIG. 3B. Everting filter 90, having the alternate everting distal region, has one advantage which may be apparent from inspection of FIG. 3B. In particular, everting filter 90 can have a very low profile or distal outer diameter when in the configuration of FIG. 3B. It is not necessary for filter body 70 to extend distally from within distal ring 64, everting, then extending proximally back over shaft 80. The embodiment of FIG. 3B can be useful where an extremely low profile distal region is required, for example, for traversing narrow and/or tortuous distal vessel regions.

FIG. 3C illustrates another embodiment of the invention in everting filter 94. Filter 94 includes referenced features previously discussed. Everting filter 94 includes a more conical shape than that of the embodiments previously discussed. Everting filter 94 also illustrates the mode of attachment of filter body to shaft in one preferred embodiment. Filter body 70 includes interior surface 72 and exterior surface 68, previously discussed. Exterior surface 72 may be seen facing and mated to shaft exterior surface 85, using methods previously discussed. Distal ring 64 is further disposed about both filter body 70 and shaft and distal region 81. The filter body surface non-everted region 76, distal-most region 78, and everted region 82 may be seen. Everted cavity 83 may also be seen, being very small in FIG. 3C. FIG. 3C illustrates a constrained configuration of everted filter 94, which would more fully evert, increasing the volume of everted cavity 83 and length of everted region 82, should filter 70 be allowed to distally travel to an unconstrained configuration.

FIG. 3D illustrates the distal region of another everting filter 96. Filter 96 includes referenced features previously discussed. Everted cavity 83 may be seen formed by everted region 82 and distal-most region 78. The shape of everted cavity 83 may be seen to be widely separated, formed by a funnel shape to the everted surface walls, where the funnel shape diverges outwardly over the length of the cavity. In particular, the minimum inside diameter of everted cavity 83 is indicated at D5. This minimum inside diameter D5 may be seen to be approximately equal to that of D4, the outside diameter of shaft 80. In the embodiment illustrated, the everted cavity minimum inside diameter is not less than that of the shaft outside diameter, and in some embodiments, can be much greater than the shaft outside diameter.

FIG. 3E illustrates yet another embodiment of the invention in everted filter 98. Filter 98 has a much less separated everted cavity 83 than that of FIG. 3D. In particular, while the walls of the everted cavity may be seen to diverge over the cavity length in FIG. 3D, the embodiment of FIG. 3E shows the walls distally converging, then diverging. The everted cavity minimum inside diameter is indicated at D7. D7 may be seen to be significantly less than outer diameter D4 of shaft 80.

FIG. 3F illustrates still another embodiment of the invention in everted filter 99. Everted filter 99 includes referenced details previously discussed with respect to other embodiments. Everted filter 99 also includes a distal tip 97, terminating in an atraumatic and preferably radiopaque safety tip 95. Distal tip 97 may be useful for insinuating the everting filter into narrow and/or tortuous vessel regions. In particular, distal tip 97 may be used to at least partially align everting filter 99 with the desired orientation indicated by the at least partially insinuated distal tip 97.

Tips can be metallic, and formed of Nitinol, stainless steel, Elgiloy or other springy materials, mono-filament or multi-filament, for example, stranded or cable. The tips can be tapered or have a uniform diameter over their length. Tips can have a circular, flat, or other cross-sectional shape. The tips can be single member or multi-member, for example, parallel independent structures. Tips can be coiled and polymer coated as well as tubular and having a slippery coating.

Some tips are entirely polymeric, for example, formed of engineering polymer, PEEK, polyimide, polyester, PTFE, and the like. Polymeric tips can be reinforced with metals or stiff polymers in the form of braids, coils, sheets, ribbons, and the like. Tips can be partly or entirely constructed of ceramics. The tips are preferably made radiopaque by means of the metal chosen or by means of radiopaque additions such as fillers added to polymer based tips.

FIG. 4A illustrates an everting filter device 100, including a filter body 70, previously discussed. Everting filter device 100 includes a first or proximal shaft 102 fixedly attached to filter body 70 with proximal ring 110. In the embodiment illustrated, a portion of filter body 70 is secured to proximal ring 110. In one example, a portion of filter body 70 may be pulled through a channel in proximal ring 110 and secured within. In another example, a portion of filter body 70 may be secured to the outside of proximal ring 110. In yet another example, a portion of filter body 70 may be disposed within ring 110, between the ring inside wall and the inserted proximal shaft distal end 106.

Filter body 70 may be seen to have a proximal mouth region 114 defining proximal opening 112 therein. In some embodiments, proximal mouth region 114 may be formed of the knitted proximal extent of filter body 70. FIG. 4A illustrates how a tubular filter body may be used to form the present invention, by utilizing the existing proximal filter body opening of the filter body as the everting filter proximal opening. This may be contrasted with using the existing filter body proximal opening to secure the filter first end region about the proximal shaft, thereafter creating the proximal opening by extremely enlarging at least one of the mesh pores. Filter body 70 first end region 62 may thus be secured using a small portion of pre-existing proximal mouth region 114.

In a preferred embodiment, the proximal opening is made by constraining the ends of a braided tube with bands, then forcing a pointed mandrel through the wall of the braid near the proximal band, and heat setting the braid to this configuration. The mandrel can have a tapered end which forces a pore opening wider as the mandrel is inserted further. The mandrel can also be worked within the selected pore to increase the size. Some methods of forming a proximal opening are described in U.S. Pat. No. 6,325,815, and in U.S. Published patent application No. 2002/0004667, both herein incorporated by reference.

A second or distal shaft 104 may also be seen, having a distal end region 108 secured to filter body second end region 60 using distal ring 64. The relative locations of proximal ring 110 and distal ring 64 to each other can change the size of everted cavity 83 and the length or amount of everted filter material 82. Either shaft 102 or 104 may be solid shafts or have lumens therethrough, depending upon the embodiment.

In some embodiments, both proximal shaft 102 and distal shaft 104 may be slidably disposed within a tube or otherwise mounted in a side-by-side slidable relationship to each other. The use of the terms proximal and distal to refer to shafts 102 and 104 respectively are used for explanation, and refer to the configuration resulting in the everted filter, as shown in FIG. 4A. It should be understood that, in the example of FIG. 4A, distal shaft 104 could be retracted proximally of proximal shaft 102.

FIG. 4B illustrates an everting filter device 120, including many of the referenced elements of FIG. 4A, which may be understood with reference to the discussion of FIG. 4A. Everting filter 120 includes proximal shaft 102 and distal shaft 104 as previously discussed. Everting filter device 120 can further include a ring or collar 122 which, in various embodiments, can be fixedly attached to either of proximal shaft 102 or distal shaft 104, but not both. The shaft which is not fixedly attached to collar 122 is preferably slidably received within collar 122. Collar 122 thus allows one shaft to be maintained in at least a partially, controlled and parallel configuration relative to the other shaft. One shaft may be held stationary while the other shaft is slidably translated through collar 122. In FIG. 4B, proximal shaft 102 is illustrated as fixed to collar 122 while distal shaft 104 is illustrated as being slidably received within collar 122.

FIG. 4C illustrates an everting filter device 124 including filter body 70 secured to distal shaft 104 at distal region 108 with distal ring 64. Everted distal cavity 83 may be seen, as previously discussed. Filter body 70 includes proximal mouth region 114 and proximal opening 112. In everting filter device 124, distal shaft 104 is disposed within a lumen 128 within proximal shaft 102. Proximal shaft 102 may be seen to terminate distally at a proximal ring 126. Proximal ring 126 may be seen to secure filter body 70 to proximal shaft 102. In filter device 124, the degree of eversion of filter body 70 may be controlled by slidably translating distal shaft 104 within proximal shaft 102.

In some embodiments, as will be further discussed, proximal mouth region 114 can be reinforced with a proximal loop. The proximal loop can be threaded through at least one portion of filter body 70. In some embodiments, filter body 70 may not be sufficiently strong or biased to expand radially and may rely at least in part on the self-expanding nature of the proximal loop. Some suitable proximal loop designs are described in European Patent Document No. EP 1181900, herein incorporated by reference.

FIG. 5A illustrates an everting filter device 130, similar in some respects to everting filter device 120 of FIG. 4B. Device 130 includes proximal shaft 102, distal shaft 104, collar 122, and filter body 70, all as previously discussed. Everting filter device 130 differs from device 120 of FIG. 4B in the curved shape of the distal portion of distal shaft 104. Distal shaft 104 includes an intermediate region 131 disposed proximal of collar 122. Intermediate region 131 may be seen to be parallel with proximal shaft 102 and, in this region, directly in line with the proximal portion of distal shaft 104. Distal shaft 104 may be seen to include a first region continuing distally past collar 122, indicated at 132. This region may be seen to extend distally from distal shaft region 131. Continuing further distally, a transverse section 132 continues transversely away from the longitudinal axis of proximal shaft 102, extending more toward the center of filter body 70 interior. Continuing distally from transverse region 134, a distally extending region 136 may be seen, which extends substantially parallel to proximal shaft 102 and distal shaft intermediate region 131.

It may be seen from inspection of FIG. 5A that curved or transverse region 134 can act as a limit to the proximal travel of distal shaft 104. Transverse region 134 may be seen to extend at a first, proximal elbow or transition region 138, and then extend transversely and distally toward a second, distal elbow or transition region 140. In some embodiments, transverse region 134 may extend perpendicular to proximal shaft 102 and distal shaft region 131. In the embodiment illustrated, transverse region 134 extends transversely while extending distally. The transversely extending or curved distal region shafts of the present invention can serve to center the filter bodies.

As distal shaft 104 is withdrawn proximally, elbow 138 will ultimately be drawn to contact collar or stop 122. At this point, further proximal travel of distal shaft 104 will be prevented or at least hindered, depending on the embodiment. In some embodiments, this serves to limit the proximal travel and limit the degree of eversion of the filter body. In other embodiments, first elbow 138 can serve to provide the treating physician with tactile feedback as to the degree of eversion. In some embodiments, transverse region 134 can be retracted through collar 122, after a threshold degree of tensile force is applied to distal shaft 104. Transverse regions such as transverse region 134 can thus serve to control the degree of filter eversion and can act to prevent the inadvertent over-eversion, reversing the relative locations of the distal and proximal regions. In some embodiments, elbows 138 and 140 are heat-set and biased to assume the shape illustrated in FIG. 5A, but are sufficiently malleable to allow transverse region 134 to be fully retracted through collar 122. This aspect can be useful where a small profile is desired for delivery, followed by the expansion to the unconstrained configuration illustrated in FIG. 5A.

Figure 5B:
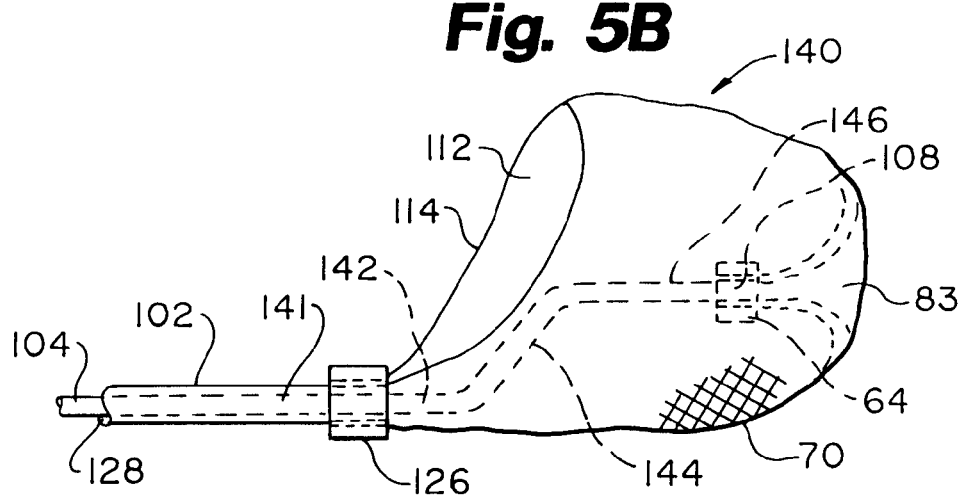
FIG. 5B is a fragmentary, perspective view of an everted filter device similar to that of FIG. 4C, but having a curved distal shaft.

FIG. 5B illustrates another everting filter device 140, which is similar in many respects to everting filter device 124 of FIG. 4C. Everting filter device 140 shares many of the aspects of device 124 of FIG. 4C, and uses the same reference numerals to describe these aspects. Everting filter device 140 includes proximal shaft 102 having a lumen 128 therethrough which slidably receives distal shaft 104. Proximal shaft 102 extends distally to proximal ring 126 which secures filter body 70 to the proximal shaft. Filter device 140 differs from filter device 124 in having a curved or transverse region 144 in distal shaft 104. Distal shaft 104 includes a region 141 disposed proximal of proximal ring 126, extending distally to a first region 142 disposed distally of proximal ring 126 and in line with distal shaft region 141 and proximal shaft 102. Continuing distally, distal shaft 104 includes a transverse region 144 which extends distally and transversely away from proximal shaft 102. In some embodiments, transverse region 104 extends perpendicularly and transversely away from proximal shaft 102. In the embodiment illustrated in FIG. 5B, transverse region 144 extends distally while extending transversely more toward the center of the filter body interior.

Continuing distally, distal shaft 104 has a third region 146 extending distally from transverse region 144 and substantially parallel to proximal shaft 102 and distal shaft region 141. Transverse region 144 can serve the same purpose as transverse region 138 of device 130 in FIG. 5A. Specifically, transverse region 144 can serve to limit the proximal travel of distal shaft 104, thereby limiting the degree of eversion of filter body 70. Transverse region 144 can also serve to provide tactile feedback to the treating physician as to the configuration of the everting filter body.

Figure 5C:
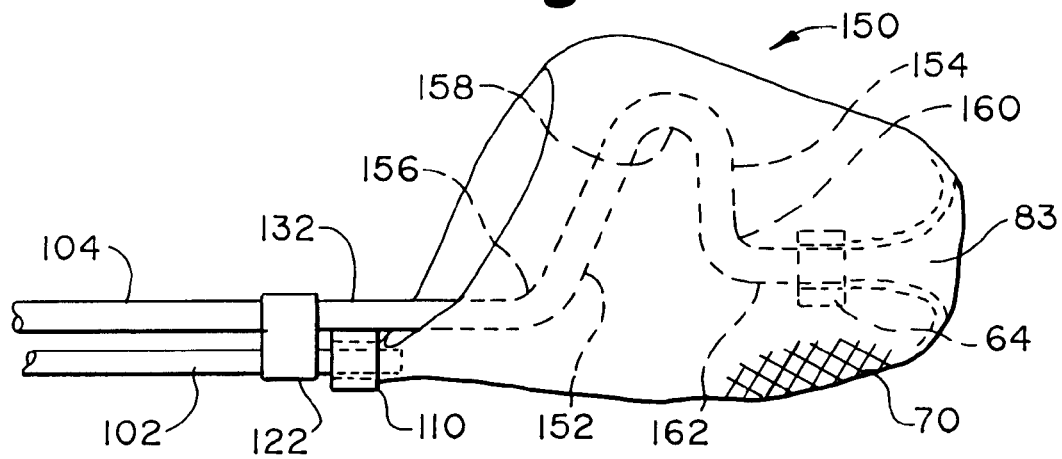
FIG. 5C is a fragmentary, perspective view of an everting filter similar to that of FIG. 5A, with a doubly curved distal shaft.

FIG. 5C illustrates yet another embodiment of the invention in everting filter device 150. Device 150 is similar in many respects to device 130 of FIG. 5A. Device 150 shares many of the same aspects of the invention as device 130 and utilizes identical reference numbers in referencing these aspects. Everting filter device 150 includes distal shaft 104 having region 132 as discussed with respect to device 130. Continuing distally, distal shaft 104 passes through an elbow 156 then to a first transverse region 152, which extends transversely away from proximal shaft 102 while extends distally away from shaft 102. Distal shaft 104 then passes through a second elbow 158, then extends distally away from proximal shaft 102 while extending transversely back toward proximal shaft 102.

Distal shaft 104 then continues along a straight region 162, then joining distal ring 64. Distal shaft 104 may be seen to have a first transverse region 152 which extends transversally past a center line of filter body 70 and transversally past a center line drawn through distal ring 64. Distal shaft 104 then doubles back and extends back toward the direction from which it came. The u-shape to the distal shaft region within filter body 70 can serve to provide tactile feedback and as a limit or restraint on proximal travel of distal shaft 104 as previously discussed. The extreme degree of transverse travel of transverse region 152 can also serve to provide some structural support for filter body 70 in the open position, and can act to open filter body 70 where the filter body itself may benefit from assistance in maintaining or re-attaining the open shape, for example, after being constrained within a delivery catheter or device.

Figure 6:
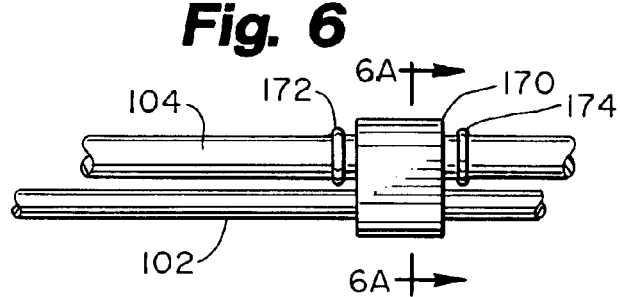
FIG. 6 is a fragmentary, side view of one frictional lock device included in some everted filter device devices.

FIG. 6 illustrates in more detail one embodiment of a frictional lock which can be used with the present invention. A frictional lock 170 is provided, and can be used in place of collar 122, depicted in FIG. 5A. Distal shaft 104 and proximal shaft 102 are illustrated as before. A proximal ring 172 and a distal ring 174 are illustrated disposed of either side of frictional lock 170. The relative sizes of the proximal and distal rings are not necessarily to scale. The relative locations of proximal and distal rings 172 and 174 relative to frictional lock 170 are also not necessarily to scale.

Figure 6A:
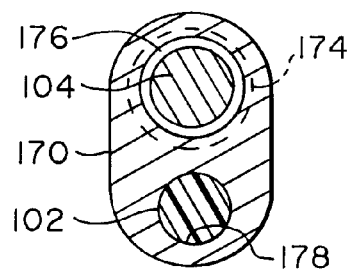
FIG. 6A is a transverse, cross-sectional view taken through 6A of FIG. 6.
Figure 6B:
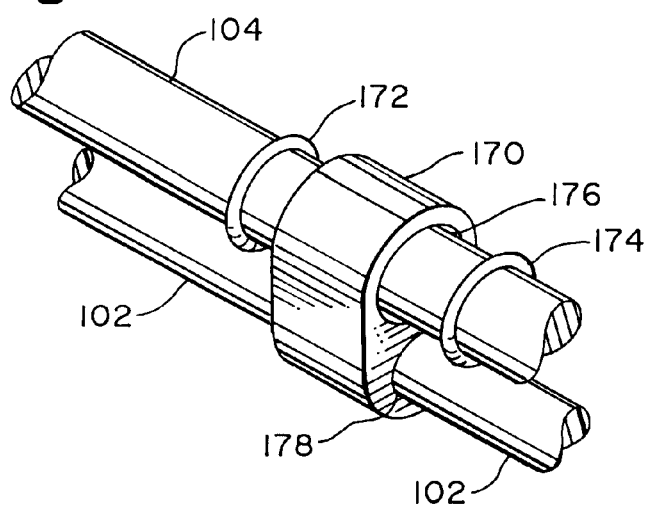
FIG. 6B is a perspective view of the frictional lock of FIG. 6.

In some embodiments, the rings 172 and 174 are disposed significantly further apart than illustrated in FIG. 6, and can serve as the distal and proximal limits to travel of distal shaft 104, and therefore the limits to the degree of eversion of filter 70. In other embodiments, rings 172 and 174 may be closer together. FIG. 6A illustrates frictional lock 170, having distal shaft 104 inserted through a top lumen 176 and filter body shaft 102 inserted through a bottom lumen 178. In one embodiment, proximal shaft 102 is fixedly secured within bottom lumen 178, and is not free to slide. Distal shaft 104 is disposed of top lumen 176, being free to slide actually through the lumen. Distal ring 174 may be seen as exceeding the diameter of lumen 176 and preventing or inhibiting travel therethrough. FIG. 6B further illustrates lock 170 in a prospective view.

In some embodiments, rings 172 and 174 do not serve to limit the travel the distal shaft 104, but instead provide resistance to travel when exceeding either ring travel limit. In particular, the rings may serve to provide a perceptible bump, giving tactile feedback to the treating physician that a limit has been exceeded. In these embodiments, the limit of travel of the rings may be exceeded prior to deployment of the filter, for example, while the filter is constrained within the delivery device or sheath. A frictional lock such as lock 170 may be used on either the distal or proximal shaft and may also be disposed at the proximal end of the device in some embodiments. The rings may be replaced in some embodiments with more gradual bulges or raised regions.

A lock is formed by the bent wire regions 138/140, and 156/158 in FIGS. 5A and 5C respectively. When the bent wire is pulled into the collar the wire will resist straightening, and a frictional force of the wire against the collar will effectively lock the wire/mesh relative to the collar/other wire.

Figure 7:
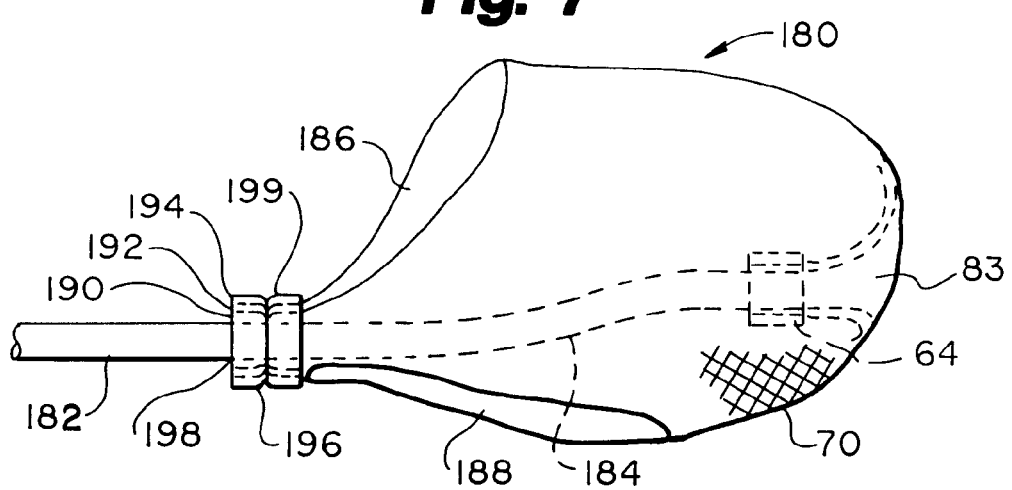
FIG. 7 is a fragmentary, perspective view of an everted filter device having a slidable proximal ring and two proximal filter body openings.

FIG. 7 illustrates yet another everting filter device 180 including filter body 70 as previously discussed. Everting filter device 180 includes both a first proximal opening or port 186 and a second proximal opening or port 188. The present invention may include several proximal openings for allowing fluid flow into the filter body. In one example, the filter body is formed by gathering together and securing the preexisting proximal mouth region of a tubular cylinder. Existing pores through the filter body wall may then be significantly enlarged by inserting ever larger members through the mesh. The enlarged pores are desirably heat set to maintain their enlarged shape. In these and other embodiments, it may be advantageous to form the large cross-sectional area openings of the present invention by forming 2, 3 or 4 openings through the proximal region of a filter body to thereby increase the opening surface area and distribute the openings more symmetrically about the shaft.

FIG. 7 also illustrates a proximal ring 199 useful with the present invention. Ring 199 includes an inner ring 190 which is slidably disposed over shaft 182 with a lumen 198. Filter body or mesh material may be seen gathered over inner ring 190 at 192. A second or outer ring 194 may then be disposed over gathered material 192 and inner ring 190. Outer ring 194 may then be secured to filter body material 192 and inner ring 190 through any suitable method, including crimping, as illustrated in FIG. 7.

Everting filter device 180 also illustrates shaft 182 having a distal region 184 which is biased to gradually slope away from the portion of shaft disposed proximally of ring 199. Shaft distal region 184 may be described as forming a gradual curved transition from the proximal ring to the distal ring where the distal ring is made to be transversally offset from a line drawn through the shaft proximal of the proximal ring. As may be seen from inspection of FIG. 7, the biased, distal transition region 184 can act to at least partially open filter body 70. In some embodiments, biased transition region 184 can also act to center filter body 70 within a vessel. Transition region 184 can be biased by heat setting the shaft material. In one example, shaft 182 and transition region 184 are formed of Nitinol, and are heat set to assume a gradual transversally sloping shape when unconstrained.

Figure 8A:
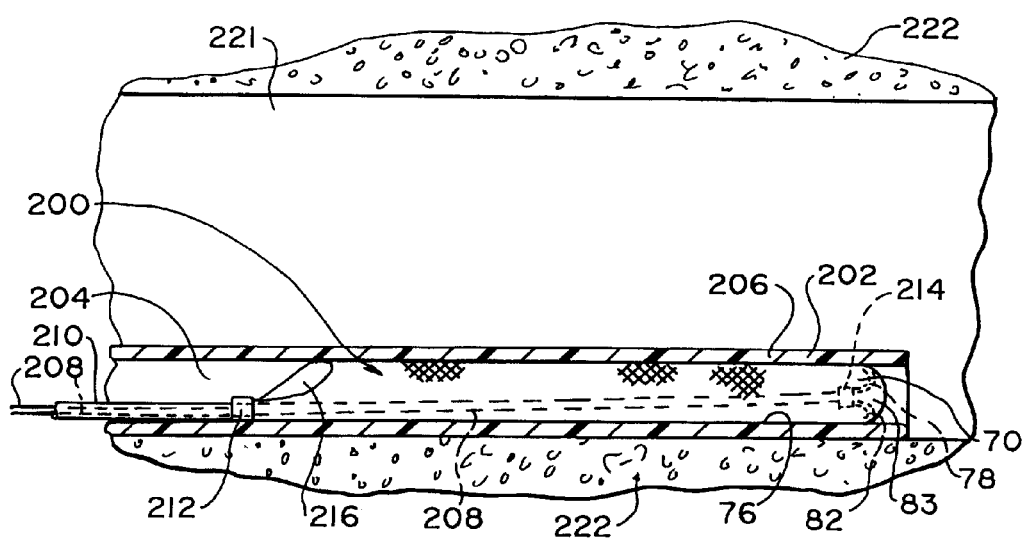
FIG. 8A is a fragmentary, longitudinal, cross-sectional view of an everting filter device similar to that of FIG. 4C shown disposed within a delivery tube prior to use.

FIG. 8A illustrates an everting filter device 200, similar in some respects, to that described with respect to FIG. 4C. Everting filter device 200 is disposed within a delivery tube or catheter 202 which is in turn disposed within a lumen 221 of a body vessel or conduit 222. Delivery tube or catheter 202 can have a distal region 206 and a lumen 204 therethrough. Everting filter device has a filter body 70 including a non-inverting exterior surface region 76, a distal-most region 78, and an everted exterior surface region 82 defining an everted cavity 83 therein. Filter body 70 may also be seen to have a first proximal opening 216. Everting filter device 200 includes a distal shaft 208 slidably disposed through a proximal shaft 210 which includes a lumen therethrough. Proximal shaft 210 terminates distally at about proximal ring 212, which also serves to secure filter body 70 to proximal shaft 210. Distal shaft 208 is secured to filter body 70 at distal ring 214. In a preferred embodiment, distal ring 214 is fixedly secured to distal shaft 208 and proximal ring 212 is fixedly secured to proximal shaft 210, but allows distal shaft 208 to axially slide through proximal ring 212. The degree of eversion of filter body 70 must thus be controlled by the relative distances between proximal ring 212 and distal ring 214, by the translating movement of shaft 208.

Figure 8B:
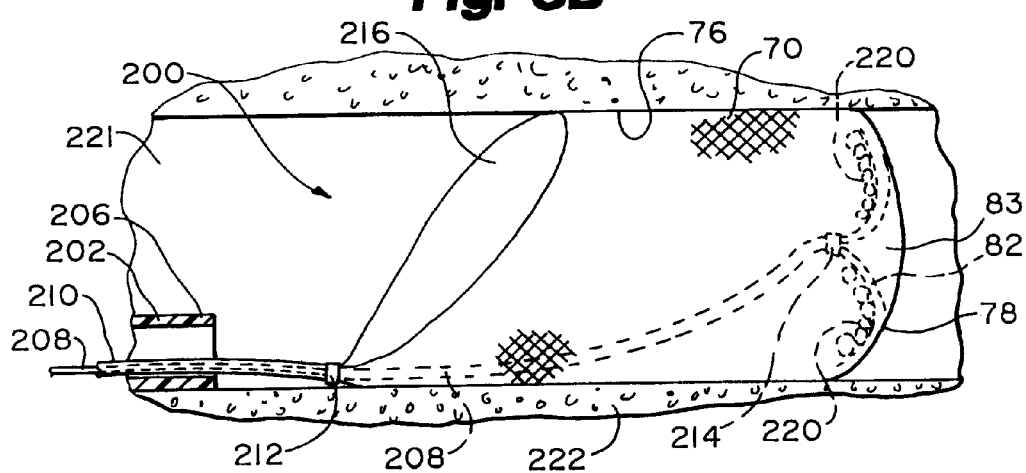
FIG. 8B is a fragmentary, longitudinal, cross-sectional view of the everting filter device of FIG. 8A, after the filter has been deployed in a vessel and at least partially occluded with filtrate material.

FIG. 8B illustrates everting filter device 200 after the device has been distally advanced from delivery catheter 202 and radially expanded and deployed within vessel 222. Vessel 222 can be any of the coronary, carotid, renal, peripheral, cerebral, neurological, and other blood vessels. Everting filter device 200 can find one exemplary and advantageous use in the narrow and tortuous neurological blood vessels. Delivery catheter 202 may, in some uses, be proximally retracted entirely from the body. Body fluid flow, for example, blood flow, may extend through filter body 70, entering through proximal openings 216, continuing through the filter, and exiting through distal-most region 78. After a period of time, filtrate material 220 may collect in the distal-most region of the filter. After sufficient time, the pressure drop across the device 200 may become too great, even totally occluding flow through the filter. In prior art devices, at this point in time, the filter would typically be proximally retracted into a capture device and removed from the body. The present invention allows changing the eversion of the filter to provide fresh, unoccluded surface area to be presented to the body fluid flow, thereby postponing the need to remove the filter device from the body, and extending the filter capacity of the device. The length of everted exterior surface material 82 may be noted in FIG. 8B.

Figure 8C:
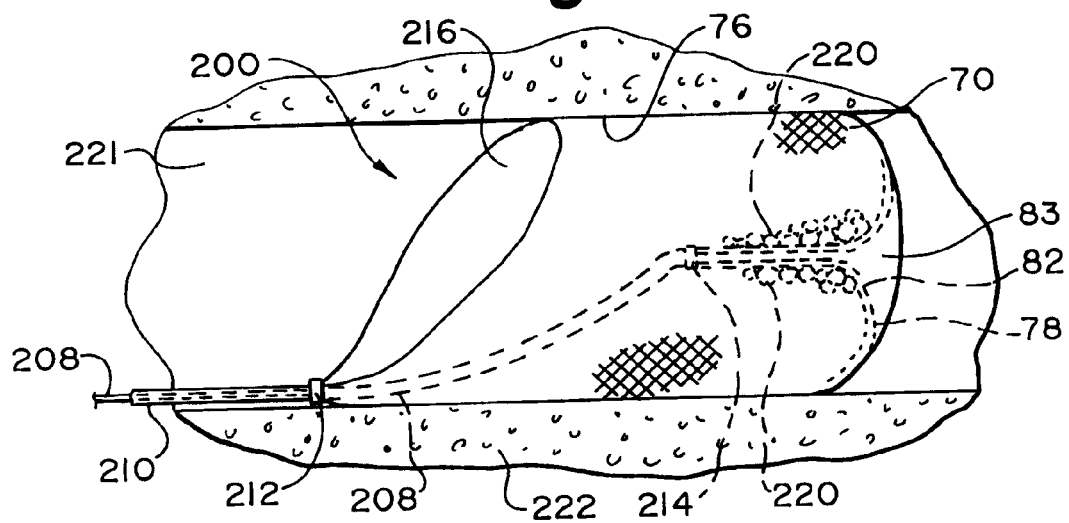
FIG. 8C is a fragmentary, longitudinal, cross-sectional view of the everting filter device of FIG. 8B, after the filter has been further everted by proximally retracting the distal ring, thereby distally advancing unoccluded filter material to the distal-most region of the filter device.

FIG. 8C illustrates everting filter device 200 after the filter has been further everted. Distal shaft 208 has been proximally retracted, thereby decreasing the distance between proximal ring 212 and distal ring 214. This also decreases the distance between the first and second ends of filter body 70. The volume of the everted cavity 83 may be seen to increase from FIG. 8B to FIG. 8C. Filtrate 220 may be adhered to the side walls of everted cavity 83. This is common in filtrate materials which tend to stick together, for example, thrombus or grumous. The length of everted filter material 82 may be seen increased from FIG. 8B to 8C as well. Distal-most region 78 of everting filter device 200 is now once again a porous region, permitting fluid flow therethrough. The present invention thus allows fresh filter media to be presented to a perfusing bloodstream without requiring the removal of the filter from the patient's body.

After a period of time, the distal-most region such as region 78 of FIG. 8C may also become occluded, and distal ring 214 proximally retracted again, further providing additional unoccluded filter material to the body fluid being filtered. This process may be continued as long as desired, or until the filtrate capacity of everting filter device 200 has been reached. The degree of eversion of filter body 70 may be either increased or decreased to present unoccluded filter material to the blood flow, depending on the device and the initial degree of eversion. At this time, everting filter device 200 can be proximally retracted into capture device, for example, into the lumen of the delivery device, such as delivery tube 202, previously discussed. Alternatively, a separate recovery catheter (not shown) can be used. In an alternate embodiment, recovery of filter device 200 is effected by extending distal shaft 208 relative to proximal shaft 210 so as to extend the filter and reduce its diameter. In this configuration, filter device 200 can be withdrawn from the body without use of a capture device.

Figure 9:
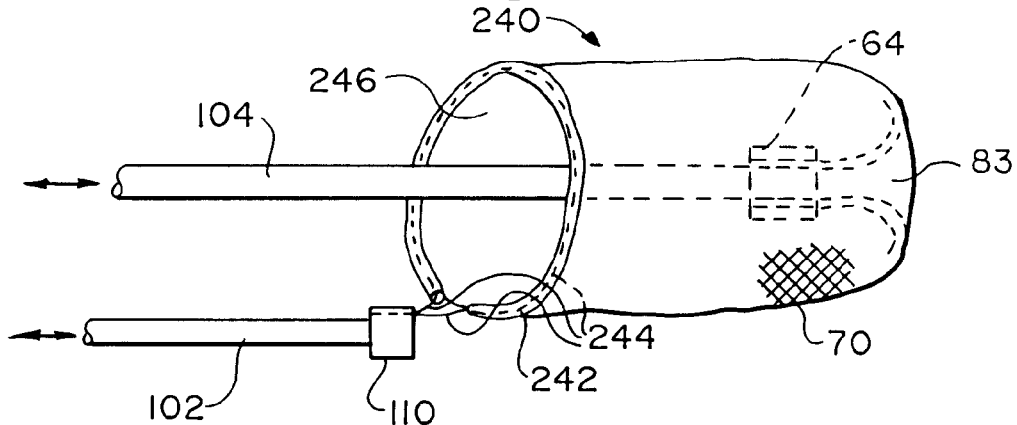
FIG. 9 is a fragmentary, perspective view of an everting filter device having a proximal shaft secured to the filter body mouth region with a filament or string.

FIG. 9 illustrates another everting filter device 240, similar in some respects to everting filter device 100 of FIG. 4A. Everting filter device 240 includes the proximal shaft 102 and proximal ring 110 previously discussed, as well as distal shaft 104 and distal ring 64. Filter body 70 includes distal everted cavity 83. Device 240 further includes a proximal opening 246 defined within a proximal mouth region 242. Proximal mouth region 242 may be seen to include a proximal loop 244 within. Proximal loop 242 may be seen to extend around the circumference of proximal mouth region 242 and be secured to proximal ring 110. In embodiments where the proximal mouth region has been formed by piercing the filter sidewall as previously discussed, the loop can remain secured in the filter body by simply intertwining the loop in the filter. In devices where the proximal mouth region has been produced by cutting the filter such that loose ends of filter strands are present, it will be desirable to weld, bond, or otherwise join at least some of the filter body strands so as to prevent filter unraveling or separation with subsequent disconnection of the loop from the proximal mouth region.

In some embodiments, filter body 70 is of sufficient strength and is sufficiently biased outward so as to not require any support from proximal loop 244. In this embodiment, loop 244 may be a string, serving as a drawstring though proximal mouth region 242. In other embodiments, filter body 70 may require, or benefit from, an outward radial force applied to proximal mouth region 242. In this embodiment, loop 244 may be formed of a stronger, wire material. In one example, loop 244 is formed of Nitinol or another wire biased to assume a substantially circular cross-sectional profile as illustrated in FIG. 9. Loop 244 may be entirely separate from the filter body 70, being affixed only to the proximal band 110, may be intertwined with the mouth of the filter body over much of the proximal mouth region 242, or may be looped through a discreet region of the filter body, most desirable through the region of the filter body diametrically opposed to the proximal band 110. A loop may be optimally attached to distal band 64 and provide radial expansion to filter body 70. This may be particularly advantageous when filter device 240 is used near bifurcations. The loop may be attached to a separate proximal ring and interwoven through the filter. Loop 244 may serve as both a proximal mouth region expansion and supporting device, as well as a closure device should everting filter device 240 be proximally retracted within a smaller profile capture device. The loop is preferably partly or entirely radiopaque so as to facilitate visualization of the proximal mouth region under fluoroscopy. Proximal loops are discussed in detail in European Patent Document No. EP 1181900, previously incorporated by reference.

Figure 10A:
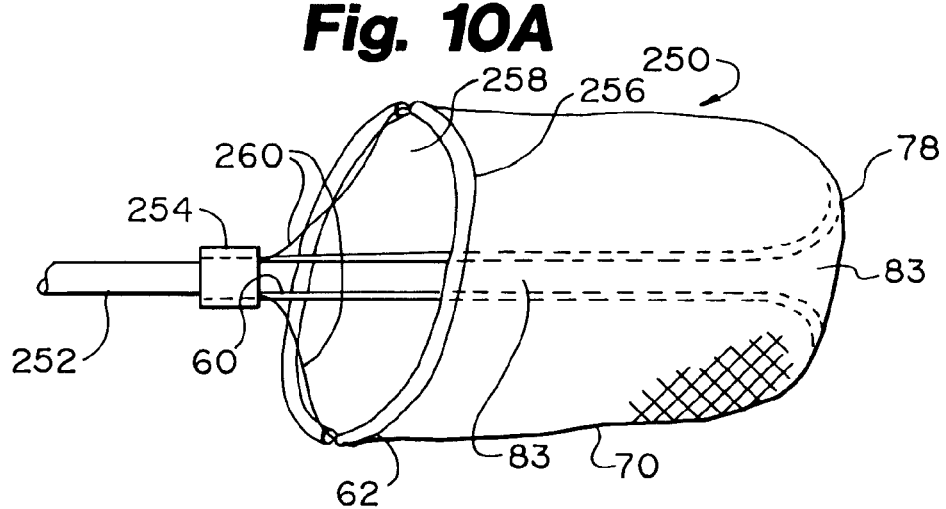
FIG. 10A is a fragmentary, perspective view of an everting filter device having the filter body everted end coupled to the shaft and the filter body proximal mouth region coupled to the shaft through fastening members.

FIG. 10A illustrates another everting filter device 250. Everting filter device 250 has only a single shaft 252 terminating in a ring or collar 254. Filter body 70 includes end region 62 terminating in a proximal mouth region 256. Filter body second end region 60 may be seen coupled directly to collar 254 and shaft 252. Proximal mouth region 256 may include a proximal loop or string within, as previously discussed, in this figure shown intertwined in the filter body 70 and not attached to collar 254. Everting filter device 250 further includes fastening members 260 coupling shaft 252 to filter body 70 via collar 254 and proximal mouth region 256. In one embodiment, fastening members 260 are struts, having significant strength in compression, and are coupled to a proximal loop disposed about mouth region 260. Struts 260 can thus act to maintain filter body 70 in an open position, thereby maintaining the patency of the proximal opening 258. In some embodiments, struts 260 are biased to splay outwardly or to assume an arcuate position when unconstrained. Support members or struts 260 can thus serve to radially expand filter body 70 when deployed from a filter delivery device.

Figure 10B:
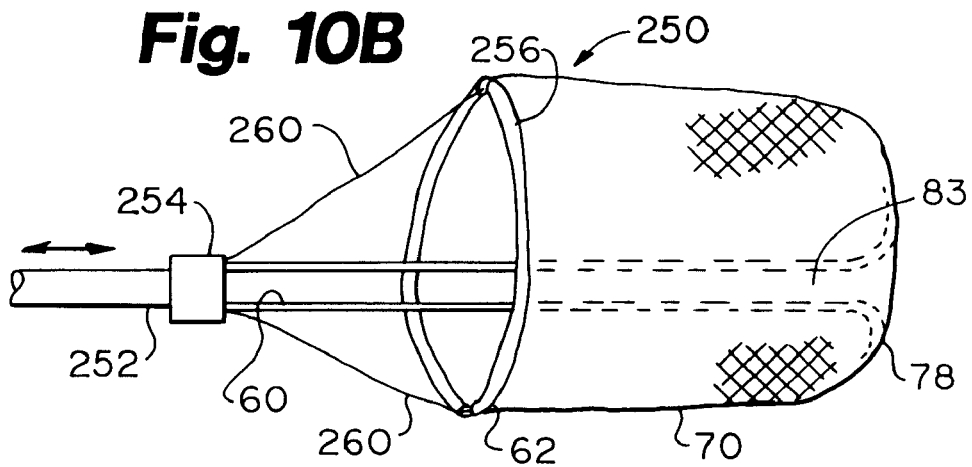
FIG. 10B is a fragmentary, perspective view of the everting filter device of FIG. 10A in the fully everted position, where the fastening members are tethers.
Figure 10C:
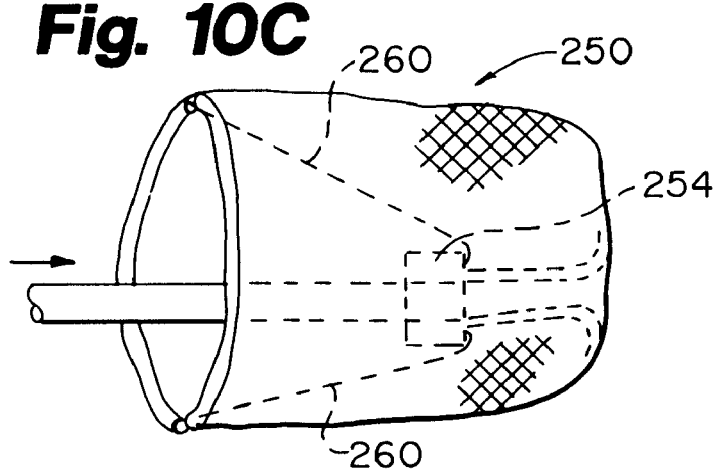
FIG. 10C is a fragmentary, perspective view of the filter device of FIG. 10B, shown in a less everted position.

FIG. 10B illustrates everting filter device 250 in a maximally everted state, where filter body second end region 60 is proximally retracted and fastening members 260 are proximally extended. FIG. 10C illustrates everting filter device 250 where shaft 252 has been maximally distally extended, thereby changing device 250 to the minimally everted state. Support members 260 may be seen as taut and maximally distally deployed. Where fastening members 260 are tethers, device 250 may be deployed in configurations intermediate those of 10B and 10C, thereby gradually increasing or decreasing the degree of eversion of filter 70. Device 250 may find one use where proximal mouth region 250 would expand radially outward beyond the vessel boundaries, thus fixing the location of the filter within the vessel and providing support for maintaining the filter position as filtrate is collected within the filter interior. In particular, as more filtrate is collected, device 250 may be gradually switched from the configuration of FIG. 10C to that of FIG. 10B. Device 250 may then be proximally retracted into a capture device, with fastening members 260 assisting in closure of proximal mouth region 256 as the filter is retracted and proximal opening 258 is closed. Device 250, as shown in FIGS. 10B-10C, further illustrates that filter body 70 can maintain a stable position in a vessel despite large motions of shaft 252.

Figure 11:
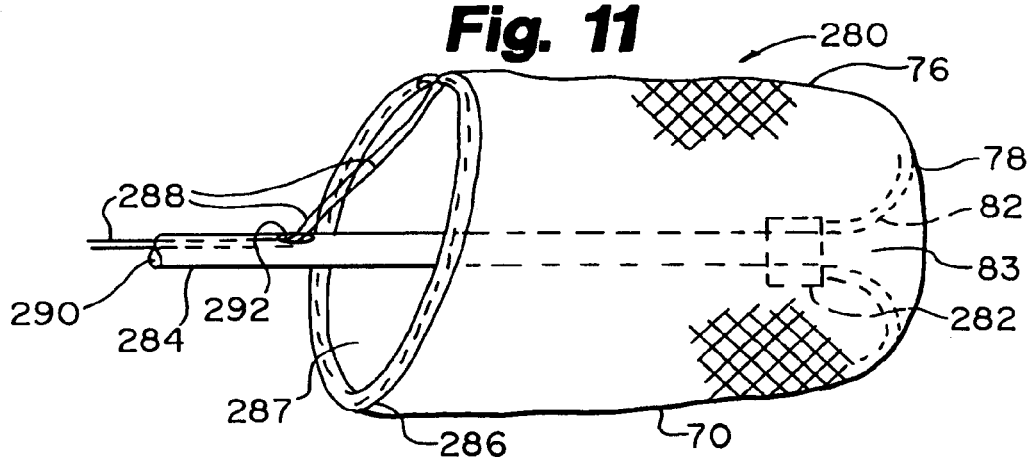
FIG. 11 is a fragmentary, perspective view of an everting filter device having a central tube, a proximal filter body mouth region, and pull strings threaded through the proximal mouth region and central tube.

FIG. 11 illustrates an everting filter device 280 having a shaft 284 terminating distally in a distal ring or band 282 which secures the second end region of filter body 70 to shaft 284. Filter body 70 has a proximal mouth region 286 having at least one drawstring 288 threaded therethrough. In the embodiment illustrated, drawstring 288 is threaded through proximal mouth region 286. Shaft 284 has a lumen 290 therethrough. Shaft 284 further includes a port 292 extending from the shaft exterior to lumen 290. Drawstring 288 extends from proximal mouth region 286 through port 292 and proximally through lumen 290 of shaft 284.

In use, filter body 70 can be constrained and significantly radially reduced in profile to fit within a delivery sheath or other delivery device. In some methods, drawstrings 288 will be pulled taut and proximal, substantially reducing the profile of proximal mouth region 286 as well. In one embodiment, filter body 70 is sufficiently outwardly biased and firm so as to not require the outward biasing force of a loop within proximal mouth region 286. Filter body 70 can be released or distally ejected from the filter delivery device and allowed to expand radially outward within the body vessel or conduit to be filtered. In one method, proximal mouth region is dimensioned to have an unconstrained diameter greater than the diameter of the vessel region to be filtered. Filter body 70 preferably has a nominally cylindrical shape where the majority of the cylinder also has a unconstrained diameter greater than the diameter of the vessel region to be filtered. The unconstrained filter body 70 is thus allowed to expand outwardly against the vessel walls, while still exerting some force and thereby at least partially anchoring filter to the vessel walls to the outward expansion force.

In some filter body embodiments, blood flow is partially or totally responsible for expanding the filter body against the vessel wall. As the distal-most region 78 becomes occluded with filtrate, shaft 284 can be retracted proximally, thereby bringing previously noneverted exterior filter surface 76 away from the vessel wall and taking the place of the distal-most region 78. In this way, unoccluded filter regions can be supplied without withdrawing the filter device from the patient. When the filter device has reached its capacity or the procedure is complete, drawstrings 288 may be used to at least partially close proximal opening 287. The at least partially closed filter device can be withdrawn from the patient's body directly or retracted into a capture device or sheath and then removed from the patient's body. Alternatively the filter device can be partially retracted into a capture device or sheath and the combination with partially unsheathed filter withdrawn from the patients body.

In another embodiment, drawstrings or tethers 288 are secured to filter body 70 at different locations about the proximal mouth region 286. Drawstrings 288 may be disposed at 180 degree, 120 degree, 90 degree, or other substantially equal distant intervals about proximal mouth region 286. An outwardly biased stiffening loop may be disposed about proximal mouth region 286 as well. In some devices, drawstrings 288 are coupled to the proximal mouth region and/or the proximal loop member. In this embodiment, another method may be practiced. The same method may be practiced in other embodiments, not requiring the stiffening proximal loop.

In this method, filter body 70 is allowed to expand after being delivered to a target vessel region to be filtered. The drawstrings 288 disposed about proximal mouth region 286 can serve to tether proximal mouth region 286 to shaft 284. The degree of eversion of filter device 270 can thus be controlled by the relative movements of drawstrings 288 within lumen 290 and the position of shaft 284. In one example, to more fully evert filter device 70 and increase the volume of everted cavity 83, shaft 284 may be proximally retracted while distally advancing drawstrings 288 through lumen 290. In this way, in some methods, the absolute position of proximal mouth region 286 within the vessel may be maintained, while proximally retracting distal ring 282 and thereby increasing the degree of eversion of filter device 70. When the filtering process is finished, drawstrings 288 may, in some methods, be used to reduce the proximal profile of proximal opening 287, followed by retracting device 280 from the patient's body. In some methods, this proximal retraction is carried out by first retracting device 280 within a filter retrieval device or sheath in whole or in part. It may be noted that in some devices, such as those having the drawstrings spaced about the proximal mouth region and having the proximal mouth region and/or filter body sufficiently biased to maintain an open shape, it may not be necessary for the filter body to expand against the enclosing vessel walls to anchor the filter device to allow control of everting.

Figure 12A:
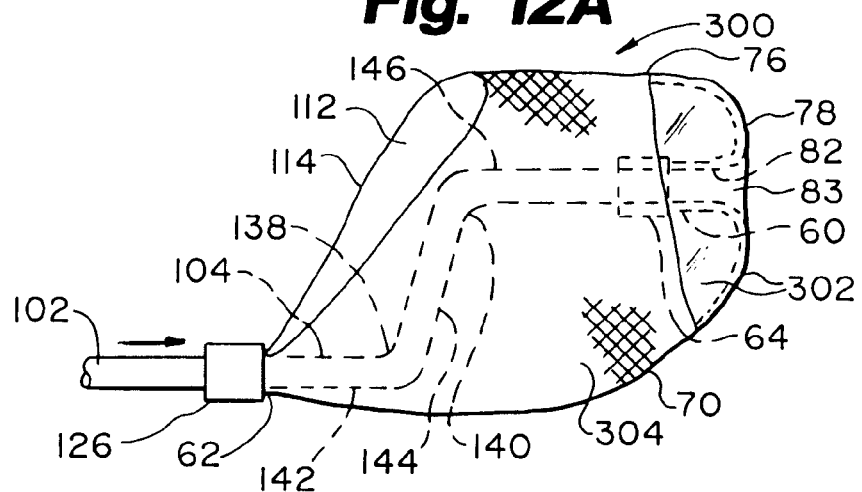
FIG. 12A is a fragmentary, perspective view of an occluding/filtering device having an occluding distal region, shown in the occluding position.

FIG. 12A illustrates a filtering/occluding device 300. Device 300 is similar in many respects to device 140 of FIG. 5B and includes many of the identically numbered elements previously described. Device 300 includes proximal shaft 102 having a distal shaft 104 disposed within, where shaft 104 includes a transverse region 144 which curves distal of proximal ring 126 and extends transversely away from proximal shaft 102. Transverse region 144 is included in some embodiments of the filtering/occluding device, but not others. Filter body 70 includes a filtering portion 304 and an occluding portion 302. In some devices, occluding portion 302 includes the same mesh materials as filtering region 304, and further includes an occluding film disposed over or within the filtering mesh material. In some embodiments, a polymeric film, for example polyurethane, silicone, latex, polyethylene, and the like is disposed over or within a wire mesh material forming the filtering portion 304.

In device 300, occluding region 302 is disposed distally of filtering region 304. Occluding region 302 is thus disposed closer to and approaches filter body second end region 60, while filtering region 304 is disposed closer to and approaches filter body first end region 62.

Filtering/occluding device 300 and most of the other filter bodies previously discussed may be considered to have a longitudinal flow channel through the device. A longitudinal flow channel may be seen entering at proximal opening 112 and continuing through the filter body interior, exiting through the filtering region 304. In configurations where the filter body is substantially completely occupying a vessel interior, flow around the device, between the device and the vessel walls, may not be possible. In such situations, the only flow through the device may be through the interior, with a substantial portion of the flow being through a proximal opening, such as proximal opening 112 in device 300. In devices some device configurations filtering region 302 is presented across substantially the entire vessel inside diameter and across substantially the entire filter device flow channel. It may be sent that in device 300, by distally extending shaft 104, occluding region 302 may expand transversely to more fully occlude a vessel device 300 is inserted within. Device 300 may thus be considered to operate by extending occluding region 302 across a vessel interior to partially, substantially, or totally occlude the vessel interior.

Figure 12B:
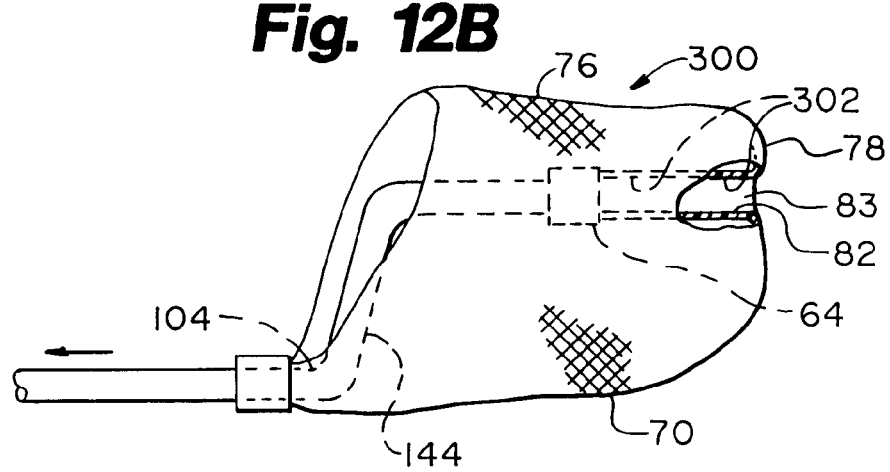
FIG. 12B shows the occluding/filtering device of FIG. 12A in a more everted, filtering position.

FIG. 12B illustrates filtering/occluding device 300, shown in a filtering configuration rather than an occluding configuration. Shaft 104, including transverse region 144, has been proximally retracted relative to the position in FIG. 12A. Filter body 70 has been more fully everted, bringing filter body material previously disposed along the side to the distal-most portion and to the everted cavity interior. The volume of everted cavity 83 may be seen to be greater, and the length of the cavity greater, relative to that of FIG. 12A. Occluding region 302 may be seen to be now lining the interior of everted cavity 83. Distal-most portion 78 is now occupied by filter material rather than occluding material. By comparing FIGS. 12A and 12B, it may be sent that filtering/occluding device 300 may be switched between a filtering and occluding mode by the advancement and retraction of shaft 104.

Figure 13A:
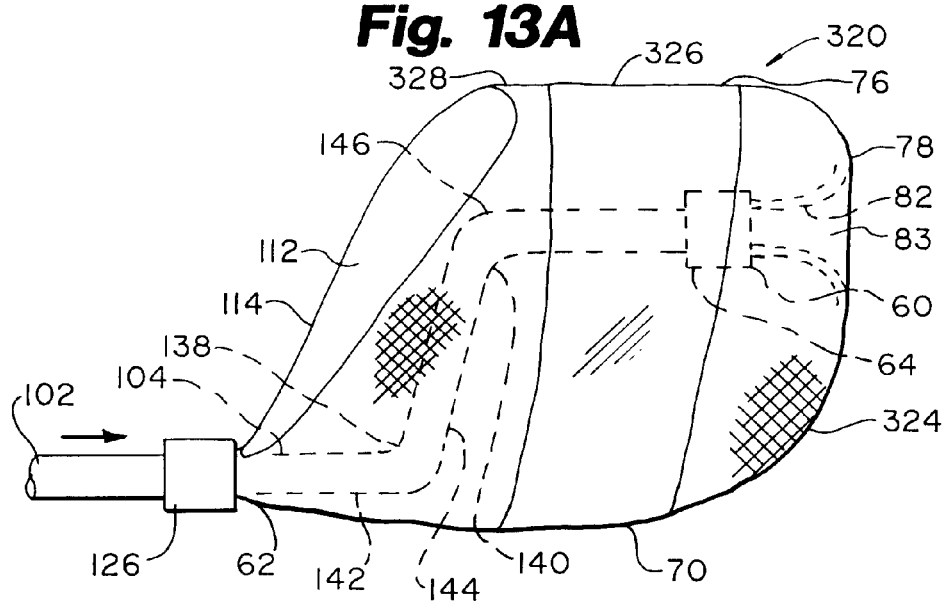
FIG. 13A is a fragmentary, perspective view of an occluding/filtering device having a filtering distal region and an occluding proximal region, shown in the filtering position.

FIG. 13A illustrates another filtering/occluding device 326. Device 326 is similar in many respects to device 300 of FIGS. 12A and 12B. In device 326, the relative positions of the occluding region and filtering region have been changed relative to those of device 300. In device 320, as illustrated in FIG. 13A, a first filtering region 324 is disposed near filter body second end region 60, with occluding region 326 disposed between the first filtering region 324 and filter body first region 62. In the embodiment illustrated in FIG. 13A, a second filtering region 328 is disposed between occluding region 326 and filter body first end region 62. In the configuration shown in FIG. 13A, fluid flow is possible through proximal opening 112 and continuing through distal-most region 78, occupied by filtering material in filtering region 324.

Figure 13B:
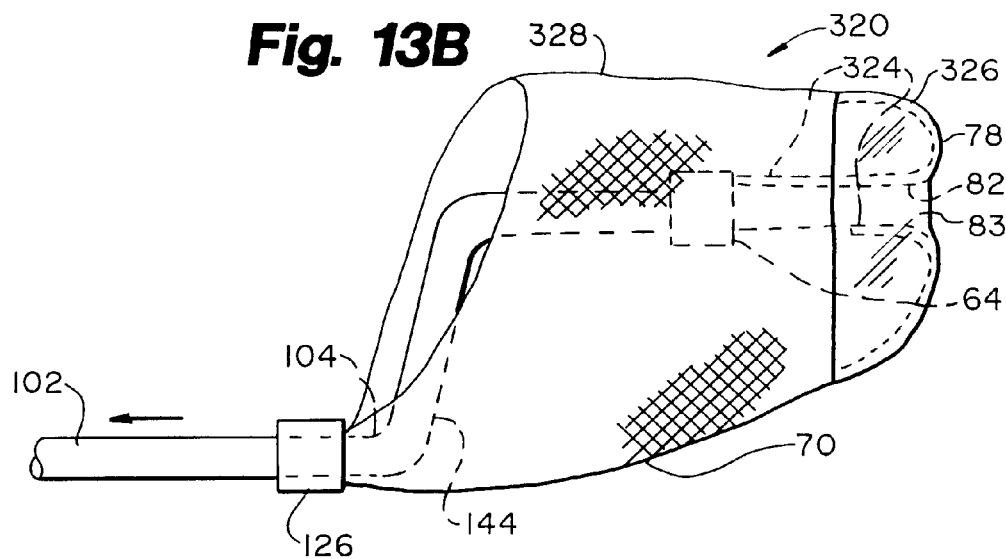
FIG. 13B is a fragmentary, perspective view of the occluding/filtering device of FIG. 13A, shown in the more everted, occluding position.

In FIG. 13B shaft 104 and transverse region 144 have been proximally retracted, thereby more fully everting filter body 70, and increasing the volume and length of everted cavity 83. It may be seen that the length of everted cavity 83 is greater in FIG. 13B than in FIG. 13A. In FIG. 13B, everted surface region 82 is occupied by filter material in filtering region 324. Distal-most region 78 is now occupied by occluding material in occluding region 326. By proximally retracting shaft 104, the filtering material disposed across the vessel cross section has been replaced by the occluding material disposed across the vessel cross section.

FIG. 14 illustrates a drug delivery device which can be used to deliver drugs, therapeutic agents, or diagnostic agents into the vessel or preferentially to the vessel wall. Agents can include restenosis inhibitors, thrombolytic agents, growth factors, biologically active proteins, and the like. Drug delivery device 340 is similar in many respects to the filtering/occluding device 300 of FIG. 12A and includes identical reference numbers for similarly described elements. In device 340, occluding region 302 may be seen to occupy everted surface region 82. Filtering region 304 may be seen to occupy the non-everted surface region 76 and distal-most region 78. Filtering region 304 thus faces vessel walls 222. Everted cavity 83 and everted region 82 may be seen to have been formed, in device 340, using the embodiment discussed with respect to FIG. 3A. In particular, everted region 82 has been formed of material heat-set or otherwise biased to form an everted distal tip when unconstrained. Preferably the everted surface region 82 will be heat set to be nearly as large as the vessel inside diameter so as to minimize the blood volume between the surface region 82 and the surface region 76, thus localizing the delivered drug in the general vicinity of the vessel wall. In other embodiments, drug delivery devices similar to device 340 can be formed not requiring the bias to form an everting distal tip when unconstrained. Specifically, in some drug delivery devices, the configuration of FIG. 3B may be more illustrative of the unconstrained state of the drug delivery distal tip when unconstrained.

Infusion of agents through device 340 is indicated in FIG. 14 at 342. In some embodiments, a separate drug infusion tube may be added to infuse the agents. In the embodiment illustrated, an annular infusion lumen is formed between shaft 104 and shaft or tube 102, in the lumen between the inner shaft and the outer tube. Drugs or other agents may thus be injected at a proximal location in shaft 102, exiting from or near proximal ring 62, but being substantially blocked by everting region 82 and occluding region 344 from being carried downstream. The agents, however, are free to contact vessel walls 222 through non-everted surface regions 76 which are occupied by filtering material 304.

In one method, drug delivery device 340 can be advanced to a vessel site to be treated, using methods previously described. These methods can include advancing device 340 over a guide wire and/or within the distal region of a delivery device or sheath. Device 340 can be deployed, and allowed to expand radially. In some methods, device 340 is maintained in a filtering mode until delivery of the agent is desired. This may be advantageous in the coronary blood vessels where angina would result from prolonged maintenance in the occluding mode. Device 340 may be manipulated, for example, by longitudinally moving shaft 104 to change the device mode to the occluding mode, as illustrated in FIG. 14. The agent may then be infused, for example, through shaft 102 and allowed to contact vessel walls 222. Device 340 may then be manipulated to assume the filtering mode, allowing blood flow, followed by repeated occluding.

The agent delivery step, occluding step, and the filtering or perfusing step may be repeated as often as necessary. In coronary applications, this may allow a substantial period of drug delivery more directly to the vessel walls while allowing intermittent periods of perfusing blood flow. When agent delivery is no longer desired, device 340 may be retracted proximally from the patient's body, for example, by retracting the device into a recovery catheter or sheath, as previously described.

Figure 15A:
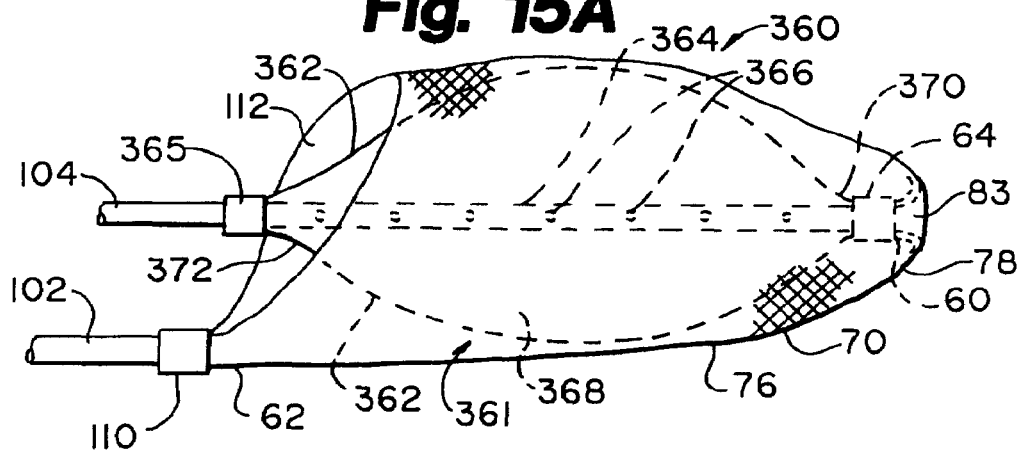
FIG. 15A is a fragmentary, perspective view of an occluding/filtering device having an inflatable balloon disposed within a mesh filter body, shown in the inflated, occluding configuration.

FIG. 15A illustrates another filtering/occluding device 360. Device 360 is similar in some respects to devices 100 and 120 illustrated in FIGS. 4A and 4B. Similar elements are referenced with reference numerals previously described. Device 360 also shares some functional and structural aspects with devices 300 and 320 of FIGS. 12A, 12B, 13A, and 13B.

Filtering/occluding device 360 includes a proximal shaft 102 coupled to the filter body first end region 62. Distal shaft 104 is coupled to filter body second end region at distal band, bushing, or ring 64. Filter body 70 may be seen to have an everted distal cavity 83, a distal-most region 78, and a non-everted surface region 76, as previously described. Device 360 also includes proximal opening 112. Device 360 includes an inflatable element, represented by an inflatable balloon 361. Balloon 361 includes a balloon envelope 362 extending to a proximal waist 372 and secured with a securing band or region 365 to shaft 104. Balloon envelope 362 also extends distally to a distal waist 370 for securing or bonding to distal ring or band 64. Balloon 361 can include an inflation tube 364 extending through the balloon interior 368 and having inflation ports 366 therethrough. In some embodiments, inflation tube 364 is a continuation of shaft 104, where shaft 104 has an inflation lumen therethrough. Balloon envelope 362 can be formed of balloon envelope material used for inflatable angioplasty balloons, well known to those skilled in the art. Typical balloon envelope materials include nylon, polyester, polyethylene, PEBAX, silicone, polyurethane, latex, and the like and may be oriented, preferably biaxially, or unoriented.

In use, device 360 may be advanced to a target site within a vessel through a delivery sheath or over a guide wire. Shaft 104, for example, may include a guide wire lumen therethrough. Rapid exchange embodiments having a separate guide wire tube and lumen extending over only over a distal region are also within the scope of the invention. When disposed at the target vessel region, balloon 362 can be inflated by providing inflation fluid through shaft 104, through inflation ports 362 and into balloon interior 368. With balloon 362 inflated, the flow channel or path through the vessel is completely or substantially blocked. In this mode, particulate flow past balloon 362 is essentially precluded. The particulate mater or filtrate may be allowed to gather proximal of inflated balloon 362 and be aspirated, removing most or all of the matter blocked by inflated balloon 362. When perfusing fluid flow or blood flow is desired, balloon 362 can be deflated and collapsed by removing the inflation fluid, and in some methods, pulling a vacuum on balloon interior on 368 through shaft 104. With balloon 362 collapsed, a perfusing fluid flow through device 360 is once again established. Particulates or filtrate not removed during an aspiration step may still be captured by filter body 70. In this way, some methods may capture much of the filtrate using the occluding, inflated balloon followed by aspiration, follow by reliance on the mesh filter material of filter body 70 to capture material which was not removed during aspiration and/or flows into filter body 70 after the aspiration step. As filtrate is captured near the distal-most region 78, filter body 70 may be further everted by proximally retracting shaft 104, as previously discussed with respect to other devices. After the filtering step or steps are complete, device 360 may be removed from the patient's body. In some methods, device 360 is removing by retracting the device proximally into a capture sheath or other device. In one method, shaft 104 may be proximally retracted during or after the filtering step or steps. Balloon 362 can be partially or fully inflated to prevent any loss of filtrate through proximal opening 112 during some or all of the retraction steps.

Filtering/occluding devices for example devices 300, 320, and 360, may be used in many applications. The filtering/occluding device may be advanced distally past thrombosed or stenosed regions to be treated. The device may be maintained in the filtering mode during periods in which only a small amount of filtrate material is expected to be carried downstream to the filtering/occluding device. When heavier material flow is expected, such as during stent expansion or balloon predilatation, the device can be manipulated into the occluding mode, ensuring almost total blockage of particulate matter from downstream travel. The material may then be aspirated, and the device manipulated back to the filtering mode.

In one use, the filtering/occluding or perfusing/occluding device may be used in the filtering or perfusing mode during radiopaque dye injection, and used in an occlusive mode for the remainder of the procedure. In another use of such filtering/occluding devices, the devices may be used primarily in either the occluding or filtering mode, depending on the judgment of the treating physician. In such use, a single filtering/occluding device may be provided for both primarily filtering or occluding uses, and physicians may choose to utilize the device for primarily the occluding or filtering modes. A single device may thus be carried which can be put to either filtering or occluding use, not requiring the stocking of both devices. The choice of a filtering or occluding device may thus be postponed well past the point of purchase and even past the point of insertion into the patient. The choice between an occluding device or filtering device may thus be made during treatment, after the filtering/occluding device has been deployed, for example, downstream of a vessel blockage to be removed.

Figure 16:
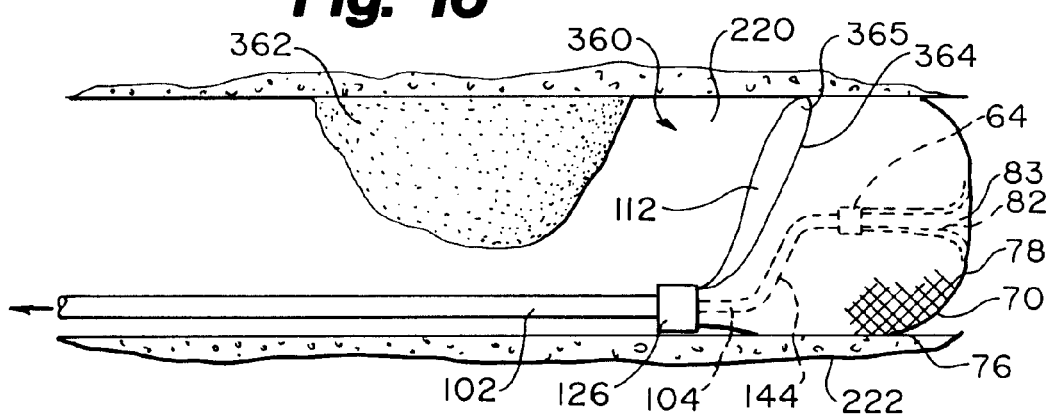
FIG. 16 is a fragmentary, longitudinal, cross-sectional view of a thrombectomy device having a proximal tube, a distal shaft slidably disposed within the proximal tube, a filter mesh filter body, and a rigid proximal loop, shown disposed distally of a thrombus.

FIG. 16 illustrates a thombectomy device 360, similar in many aspects to filter device 140 illustrated in FIG. 5B. Thombectomy device 360 includes shaft 102 coupled to filter body 70 and having distal shaft 104 slidably disposed within shaft 102. Thombectomy device 360 may be further understood by reading the description of device 140, previously described.

Thombectomy device 360 has a proximal opening 112 and a proximal loop 364. Proximal loop 364 is preferably sufficiently rigid and can be biased to expand radially outward and to maintain a sufficiently rigid shape when encountering a thrombus such as thrombus 362. In some embodiments, proximal loop 364 has a proximally leading edge sufficiently narrow or sharp to cut through or dislodge thrombus 362. In some embodiments, proximal loop 364 is formed of Nitinol wire biased to firmly engage vessel wall 222. Proximal loop 364 may be threaded through filter body 70 at location 365 indicated near vessel wall 222, opposite shaft 102. In other embodiments, proximal loop 364 may be threaded through the proximal mouth region of filter body 70 in numerous locations about the mouth region. Thombectomy device 360 may be deployed downstream of thrombus 362 using methods previously discussed, including dye catheters, and delivery tubes.

Figure 17:
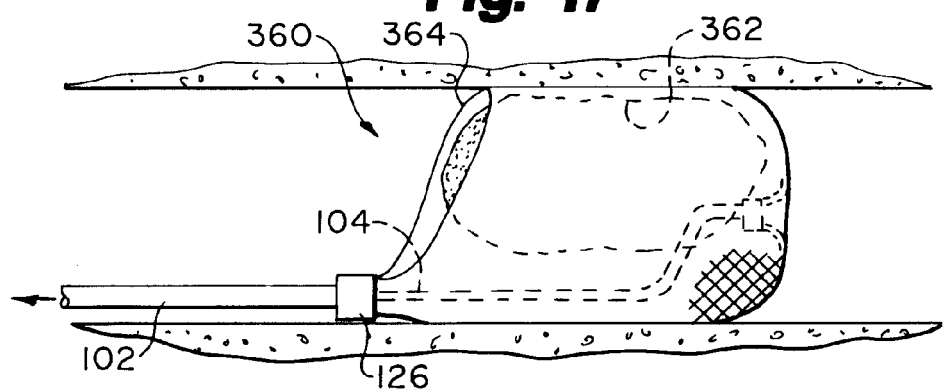
FIG. 17 is a fragmentary, longitudinal, cross-sectional view of the thrombectomy device of FIG. 16, shown after the proximal loop has dislodged the thrombus and the filter body has captured the thrombus, with the inner shaft distally extending the filter body length.

FIG. 17 illustrates thombectomy device 360 after proximal loop 364 has been pulled through thrombus 362. While shaft 102 has been proximally retracted, distal shaft 104 has been distally advanced relative to the retracting proximal shaft 102. The degree of eversion of filter body 70 may be seen to be greater in FIG. 16 than in FIG. 17. Filter body 70 has been elongated, during the capture of thrombus 362.

Figure 18:
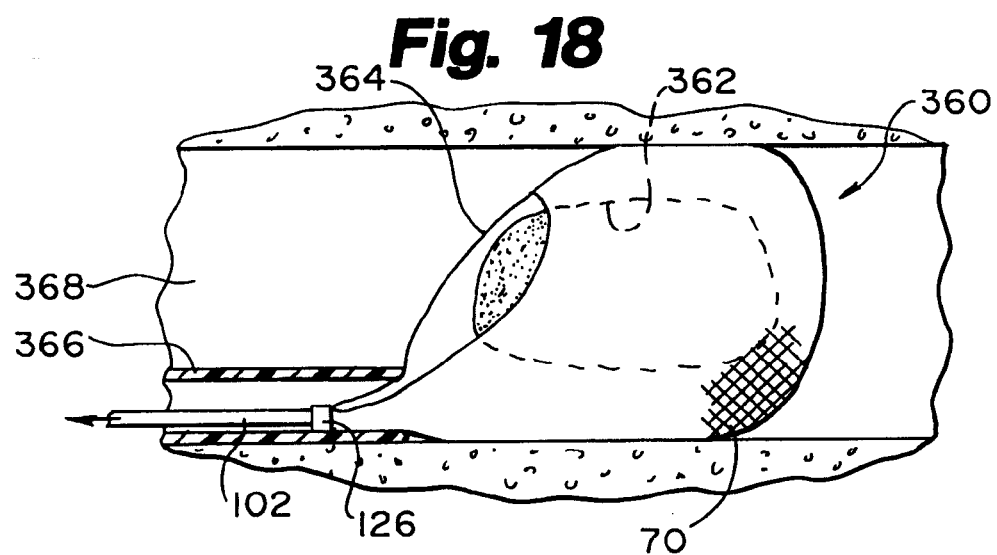
FIG. 18 is a fragmentary, longitudinal, cross-sectional view of the thrombectomy device of FIG. 17, after the thrombectomy device has been partially retracted within a capture tube distal region.

FIG. 18 illustrates thrombus 362, captured within device 360, with device 360 being retracted proximally into a capture device or tube 366 having a lumen 368 therethrough. As previously discussed with respect to other embodiments, proximal loop 364 may be at least partially closed prior to or during the proximal retraction step. The proximal mouth can be substantially closed by retraction into tube 366, and once this occurs thrombus 362 will be entirely captive within device 360.

FIG. 19 illustrates thombectomy device 360 after being proximally retracted within capture device 366. Capture device 366, thombectomy device 360, and thrombus 362 may be proximally retracted from the patient.

Figure 20A:
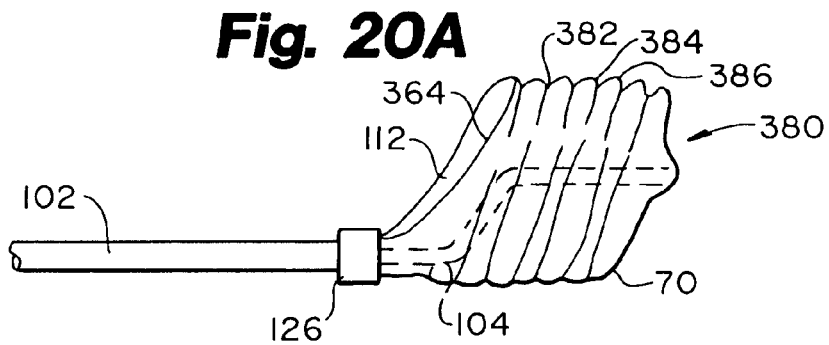
FIG. 20A is a fragmentary, perspective view of an everting filter device having a bellowed filter body, shown in the compact configuration.
Figure 20B:
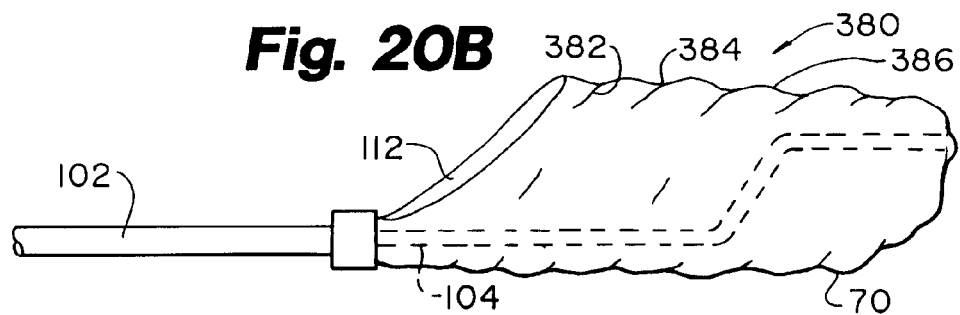
FIG. 20B is a fragmentary, perspective view of the everting filter of FIG. 20A, shown in the extended, elongate configuration.

FIG. 20A illustrates filter body 70 having a bellows shape. While filter body 380 may be used in conjunction with any of the previously discussed embodiments, one preferred use is in forming the filter body of thombectomy devices, such as thombectomy device 360. The filter body used for thombectomy devices can be formed of a polymeric film rather than a porous mesh in some devices, or by a combination of the mesh with a film. Device 380 may be seen to have a bellows configuration, having the filter body length substantially foreshortened during proximal retraction of shaft 104. The excess filter body material which will ultimately be used to extend the length of the filter may be bunched or folded upon itself along regions of preferential folding 382. Regions of preferential folding 382 may be formed by wire hoops, heat set regions, and any of a number of shape memory materials commonly known to those skilled in the art. Regions of preferential folding may also be formed by ribs set into the filter material. Regions of preferential folding 382 may be seen to form a series of valleys 364 separated by peaks 386. FIG. 20B illustrates device 380 in an elongated configuration. Device 380 can provide a high ratio between the elongated length and the shortened length. The bellows shape can provide a high ratio between filled length and deployed length.

Thrombectomy device 380 can be deployed through a small catheter distal to a thrombus or other blockage material. The deployed shape is preferably the shortest shape so as to minimize the length needed for deployment. The device may be delivered within a catheter in an elongated shape and then deployed out the end of the catheter by pushing on shaft 102 while only slightly retracting the catheter so as to deploy the maximally shortened length immediately distal to the deployment catheter. Typically the catheter is then removed. Shaft 102 can be used to draw filter body 70 through the thrombus, with a proximal loop dislodging the thrombus from the vessel wall, and the thrombus entering and lengthening the filter body. The thrombus filled filter body can be partially retracted into a recovery catheter to close the proximal loop and proximal opening. The filter body can be either retracted further into the catheter or the recovery catheter retracted from the patient coupled to the partially retracted filter body. In one embodiment, the thrombectomy device of FIGS. 20A and 20B has an everted distal region. In another embodiment, the thrombectomy device of FIGS. 20A and 20B does not have an everted distal region.

FIG. 21A illustrates a proximal handle portion 400 including an outer tube 402 and an inner shaft 408. Proximal handle portion 400 can be used in embodiments having a shaft extending distally from a tube, such as the example of FIG. 4C. Outer tube 402 includes a proximal region 404 having a proximal port 406 having shaft 408 extending proximally from the tube. Shaft 408 is preferably closely fit and slidably disposed within tube 402.

FIG. 21B illustrates a proximal handle portion 410 which can be used in devices having tethers or drawstrings, for example the device illustrated in FIG. 11. Proximal handle portion 410 includes an outer tube 412 having a proximal region 414 and a lumen 413 within. A handle 416 can be slidably disposed within tube 412 and have tethers 417 attached to the handle. Handle 416 can have a proximal region 418 having an outer diameter indicated at 411, where the outer diameter can be larger than the inside diameter of the tube, and can be about 0.014 inch or larger in some embodiments. Handle 416 can also have a stepped down diameter portion 419 adapted to slidable fit within tube 412. The tethers can be proximally retracted by proximally retracting handle 416.

FIG. 21C illustrates a proximal handle portion 420 which can be used in devices having tethers or drawstrings, for example the device illustrated in FIG. 11. Handle portion 420 can have a tube 422 having a round portion 424, a more proximal cut-away portion 425, and a proximal end 423. Tethers or drawstrings 436 can be disposed within tube 422 and extend proximally from an opening 434 disposed between an insert 426 and tube round portion 424. The length of opening 434 is indicated at 432, and is preferably long enough to allow the tethers to easily egress the tube. An insert 426 can be disposed within tube 422, and can be within cutaway portion 425. Insert 425 can be formed of an elastomeric material, may be formed within and bonded to the tube, and have a slit 428 formed into the insert. Slit 428 can be used to lock down the tethers into the slit while allowing the tethers to be pulled free of the insert and proximally retracted. The outer diameter of tube 422 is indicated at 430 and can be about 0.014 inch in one embodiment. The small inside diameter and long length, nominally 145 cm, of the tube will substantially reduce or preclude any blood loss through opening 434.

FIG. 21D illustrates a proximal handle portion 440 including a tube 442 which can be used in devices having a drug delivery lumen or an inflation lumen disposed within the tube. A tee connector 441 having sidearms 452, a lumen 454, and Tuohy-Borst fittings 456 and 458 is disposed about tube 442. Tee connector 441 can include an injection port 462 which can be used to inject drugs into the connector and tube. Tube 442 can have a proximal port 446 having an inner shaft or elongate member 448 extending proximally from the tube, with the shaft extending further proximally through proximal fitting or seal 458 through a proximal port 460, terminating in a shaft proximal region 450. Shaft 448 can thus slide within tube 442. In some embodiments, port 446 is the proximal port for an annular lumen formed between tube 442 and shaft 448.

Figure 15B:
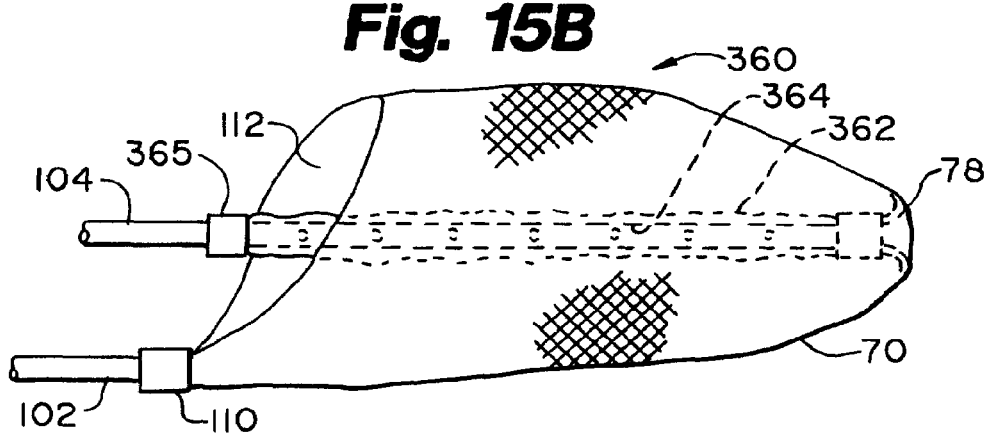
FIG. 15B is a fragmentary, perspective view of the occluding/filtering device of FIG. 15, shown in the uninflated, filtering configuration.
Figure 21E:
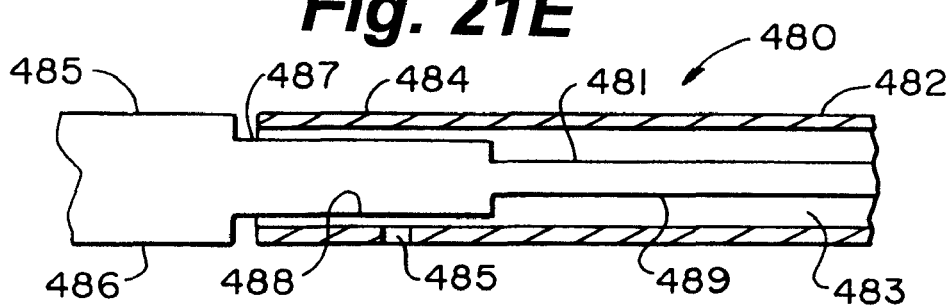
Figure 21F:
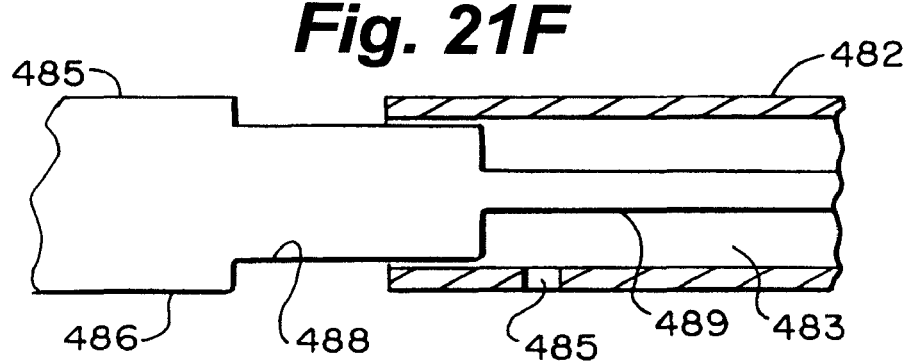

FIGS. 21E and 21F illustrate a proximal handle portion 480 including an outer tube 482 and an inner shaft 481. Proximal handle portion 480 can be used in embodiments having an inflatable balloon, such as the example of FIGS. 15A and 15B, as well as other examples of the invention. Outer tube 482 includes a proximal region 484 having a proximal port 487 with shaft 481 being proximally accessible for manipulation from outside of the tube. A handle 485 may be seen to have a large outer diameter portion 486, a stepped down portion 488 slidably disposed within tube 482, which is coupled to inner shaft portion 489. Tube 482 can have a port or microhole 485 in communication with tube lumen 483. In the configuration of FIG. 21E, microhole 485 is blocked by handle stepped down portion 488 In the configuration of FIG. 21F, microhole 485 is not blocked by the handle, which has been proximally retracted.

The porous mesh filter bodies of the present invention can be formed of strands, ribbons, or wire, where the materials forming the strands, ribbons, or wires can be metallic or polymeric. Non-limiting examples of such materials include Nitinol, stainless steel, Elgiloy, spring steel, beryllium copper, nylon, PEEK, PET, liquid crystals, polyimide, and shape memory alloys and polymers generally. Elastomeric polymers can be also be used to form the strands and filter bodies. The elastomeric polymers can be formed, shaped, or post processed to achieve the desired shape. Examples of elastomeric polymers include butyl rubber, natural rubber, latex, and polyurethanes. The strands or wires can have circular, square, rectangular, or irregular cross-sectional shapes. In one filter, the strands or wires have an outer diameter between about 0.001 inch and 0.010 inch. The mesh can be any mesh having suitable porosity for the intended use, for example, for allowing perfusing blood flow while capturing emboli. Examples meshes include braids, knits, interlocking rings or polygons, weaves, helically wound patterns, and non-woven meshes formed from chopped strand fibers. The filters can include radiopaque markers, for example, platinum wires disposed in the mesh or radiopaque coatings applied to the strands, or the strands can be composites of radiopaque and radiolucent materials disposed for example in a coaxial relationship.

The mesh filter bodies may be made using methods similar to those described in U.S. Pat. No. 6,325,815 and PCT Publication No. WO 96/01951, both herein incorporated by reference. In one method, a one-layer braided Nitinol mesh cylinder is threaded through the lumen of a forming cylinder, folded over the forming cylinder rounded nose, folded back on the outside of the forming cylinder, and heat set. This results in a pre-stressed braid that can easily recoil in a similar manner to a spring. A dense braid, having a high number of picks per inch (PPI) is preferred. One filter embodiment has between about 50 and 400 PPI.

Some meshes are selected to have an average pore size large enough to allow perfusing blood flow while small enough to capture emboli. Various meshes have average pore sizes of at least about 20, 50, and 100 microns. The meshes used for the perfusing/occluding embodiments of the invention may have larger average pore size, in embodiments intended for only perfusing and occluding rather than filtering and occluding. Some embodiments of the drug infusion device, previously described, can include a large pore size region intend to provide structure and allow drug passage rather than providing significant filtration capture capacity for emboli.

The curved or transversely extending shaft distal regions found within some filter bodies can be formed of Nitinol, heat set to assume a bent, curved, or S-shape when unconstrained. In some methods, the shaft is formed of Nitinol wire, heat set at about 600 degrees C.

The dimensions of the various everted filter devices may vary, depending on the intended application. The dimension ranges required are well known to those skilled in the art. The device dimensions may be dictated by the expected vessel inner diameters, the distance from the point of insertion to the vessel region to be treated, and the dimensions of other instruments to be used concurrently in the same vessel. In one example, filters intended for use in filtering carotid arteries are expected to be larger than those for coronary artery applications, which are likely larger than those for use in the cerebral arteries.

Some everted filter devices have elongate member lengths ranging from about 50 cm to about 320 cm. In one group of embodiments, the outer diameter of tethers range from about 0.001 inch to about 0.005 inch, the outer diameter of solid shafts range from about 0.008 inch to about 0.035 inch, and the outer diameter of tubes range from about 0.010 inch to about 0.035 inch. In some filter bodies, in the fully elongated state the length is between about 10 mm and 50 cm, while the outer diameter is between about 2 mm and 35 mm. In a fully radially expanded and shortened state, some filter bodies can have a length of between about 2 mm and 10 mm, while the outer diameter can be between about 3 mm and 38 mm. The proximal opening size may have an average width of between about 1 mm and 35 mm. In some filters, the average pore size can increase by about 5000 percent from the most compressed to the most expanded state. As used herein, the term "pore size" refers to the diameter of the largest sphere that will fit through the pore. A pore can become elongated as the mesh is elongated. The elongated pore may have a very large width and a very small height, therefore having a very small pore size.

What is claimed is:

1. A filter device for filtering a body vessel fluid in a patient's body, the vessel having interior walls, the device comprising:
   a first elongate member having a distal region; and
   a filter body having an open proximal end region and a closed everted distal end region and having a length and a volume, the filter body being coupled to the distal region of the first elongate member, the filter body being configured to be expanded within the vessel from a delivery configuration to a filtering configuration in which the filter body is expanded to a vessel engaging diameter substantially equal to an interior diameter of the vessel such that the filter body engages the interior walls of the vessel, the filter body in the filtering configuration having at least first and second filtering positions, a length of the everted distal end region in the first position being less than a length of the everted distal end region in the second position, the vessel engaging diameter of the filter body being maintained in both the first and second filtering positions, wherein the distal end region of the filter body is directly connected to a distal ring and wherein the distal ring is fixedly connected to the first elongate member.

2. The filter device of claim 1 wherein a volume of the everted distal end region in the first position is less than a volume of the everted distal end region in the second position.

3. The filter device of claim 1 wherein the proximal end region of the filter body is connected to a proximal ring.

4. The filter device of claim 3 wherein the proximal ring encircles the first elongate member.

5. The filter device of claim 3 wherein the proximal ring is slideably connected to the first elongate member.

6. The filter device of claim 1 wherein the filter body comprises a filter mesh.

7. The filter device of claim 6 wherein the filter mesh is self-expanding.

8. The filter device of claim 1 wherein the filter body has a first distal-most region in the first position and a second distal-most region in the second position, the first distal-most region being different from the second distal-most region.

9. A filter device for filtering a body vessel fluid in a patient's body, the vessel having interior walls, the device comprising:
   a first elongate member having a distal region; and
   a filter body having an open proximal end region and a closed everted distal end region and having a length and a volume, the filter body being coupled to the distal region of the first elongate member, the filter body being configured to be expanded within the vessel from a delivery configuration to a filtering configuration in which the filter body is expanded to a vessel engaging diameter substantially equal to an interior diameter of the vessel such that the filter body engages the interior walls of the vessel, the filter body in the filtering configuration having at least first and second filtering positions, a length of the everted distal end region in the first position being less than a length of the everted distal end region in the second position, the vessel engaging diameter of the filter body being maintained in both the first and second filtering positions, wherein the proximal end region of the filter body is directly connected to a proximal ring and the distal end region of the filter body is directly connected to a distal ring and wherein one of the distal and proximal rings is fixedly connected to the first elongate member.

10. The filter device of claim 9 wherein one of the distal and proximal rings is slideably connected to the first elongate member.

11. The filter device of claim 9 wherein the distal ring is spaced from the proximal ring a first distance when the filter body is in the first position and a second distance when the filter body is in the second position, the first distance being greater than the second distance.

12. A filter device for filtering a body vessel fluid in a patient's body, the vessel having interior walls, the device comprising:
   a first elongate member having a distal region; and
   a filter body having an open proximal end, the filter body being coupled to the distal region of the first elongate member, the filter body being configured to be expanded within the vessel from a delivery configuration to a filtering configuration in which the filter body is expanded to a vessel engaging diameter substantially equal to an interior diameter of the vessel such that the filter body engages the interior walls of the vessel, the filter body in the filtering configuration having at least first and second filtering positions, the vessel engaging diameter of the filter body being maintained in both the first and second filtering positions, a length of the filter body in the first position being greater than a length of the filter body in the second position, wherein the filter body has a distal end directly connected to a distal ring and wherein the distal ring is fixedly connected to the first elongate member.

13. The filter device of claim 12 wherein the proximal end of the filter body is connected to a proximal ring.

14. The filter device of claim 13 wherein the proximal ring encircles the first elongate member.

15. The filter device of claim 13 wherein the proximal ring is slideably connected to the first elongate member.

16. The filter device of claim 12 wherein the filter body has a first distal-most region in the first position and a second distal-most region in the second position, the first distal-most region being different from the second distal-most region.

17. A filter device for filtering a body vessel fluid in a patient's body, the vessel having interior walls, the device comprising:
   a first elongate member having a distal region; and
   a filter body having an open proximal end, the filter body being coupled to the distal region of the first elongate member, the filter body being configured to be expanded within the vessel from a delivery configuration to a filtering configuration in which the filter body is expanded to a vessel engaging diameter substantially equal to an interior diameter of the vessel such that the filter body engages the interior walls of the vessel, the filter body in the filtering configuration having at least first and second filtering positions, the vessel engaging diameter of the filter body being maintained in both the first and second filtering positions, a length of the filter body in the first position being greater than a length of the filter body in the second position, wherein the filter body has a distal end and wherein the proximal end of the filter body is directly connected to a proximal ring and the distal end of the filter body is directly connected to a distal ring and wherein one of the distal and proximal rings is fixedly connected to the first elongate member.

18. The filter device of claim 17 wherein one of the distal and proximal rings is slideably connected to the first elongate member.

19. The filter device of claim 17 wherein the distal ring is spaced from the proximal ring a first distance when the filter body is in the first position and a second distance when the filter body is in the second position, the first distance being greater than the second distance.

20. The filter device of claim 17 wherein the filter body comprises a filter mesh.

21. The filter device of claim 20 wherein the filter mesh is self-expanding.

22. A filter device for filtering a body vessel fluid in a patient's body, the vessel having interior walls, the device comprising:
   a first elongate member having a distal region; and
   a filter body having an open proximal end, the filter body being coupled to the distal region of the first elongate member, the filter body being configured to be expanded within the vessel from a delivery configuration to a filtering configuration in which the filter body engages the interior walls of the vessel, the filter body in the filtering configuration having at least first and second filtering positions, an outer diameter of the filter body at a location of engagement with the interior walls of the vessel being the same in both the first and the second filtering positions, the filter body having a filter mesh, a first portion of the filter mesh forming a distal-most region of the filter body and a second portion of the filter mesh engaging the interior walls of the vessel when the filter body is in the first position, the second portion of the filter mesh forming a distal-most region of the filter body when the filter body is in the second position, the second portion being different from the first portion, wherein the filter body has a distal end directly connected to a distal ring and wherein the distal ring is fixedly connected to the first elongate member.

23. The filter device of claim 22 wherein the proximal end of the filter body is connected to a proximal ring.

24. The filter device of claim 23 wherein the proximal ring encircles the first elongate member.

25. The filter device of claim 23 wherein the proximal ring is slideably connected to the first elongate member.

26. The filter device of claim 22 wherein the filter mesh is self-expanding.

27. A filter device for filtering a body vessel fluid in a patient's body, the vessel having interior walls, the device comprising:
   a first elongate member having a distal region; and
   a filter body having an open proximal end, the filter body being coupled to the distal region of the first elongate member, the filter body being configured to be expanded within the vessel from a delivery configuration to a filtering configuration in which the filter body engages the interior walls of the vessel, the filter body in the filtering configuration having at least first and second filtering positions, an outer diameter of the filter body at a location of engagement with the interior walls of the vessel being the same in both the first and the second filtering positions, the filter body having a filter mesh, a first portion of the filter mesh forming a distal-most region of the filter body and a second portion of the filter mesh engaging the interior walls of the vessel when the filter body is in the first position, the second portion of the filter mesh forming a distal-most region of the filter body when the filter body is in the second position, the second portion being different from the first portion, wherein the filter body has a distal end and wherein the proximal end of the filter body is directly connected to a proximal ring and the distal end of the filter body directly is connected to a distal ring and wherein one of the distal and proximal rings is fixedly connected to the first elongate member.

28. The filter device of claim 27 wherein one of the distal and proximal rings is slideably connected to the first elongate member.

29. The filter device of claim 27 wherein the distal ring is spaced from the proximal ring a first distance when the filter body is in the first position and a second distance when the filter body is in the second position, the first distance being greater than the second distance.

* * * * *

UNITED STATES PATENT AND TRADEMARK OFFICE
CERTIFICATE OF CORRECTION

PATENT NO. : 7,621,870 B2  Page 1 of 1
APPLICATION NO. : 11/208497
DATED : November 24, 2009
INVENTOR(S) : Berrada et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1054 days.

Signed and Sealed this

Twenty-sixth Day of October, 2010

David J. Kappos
*Director of the United States Patent and Trademark Office*